United States Patent
Loehrlein et al.

(10) Patent No.: US 6,618,679 B2
(45) Date of Patent: Sep. 9, 2003

(54) METHODS FOR ANALYSIS OF GENE EXPRESSION

(75) Inventors: Christine Loehrlein, Alameda, CA (US); Dan Pollart, Alameda, CA (US); Thomas Shaler, Fremont, CA (US); Kathy Stephens, Fremont, CA (US); Yuping Tan, Fremont, CA (US); Linda Wong, Daly City, CA (US); Joseph Monforte, Berkeley, CA (US)

(73) Assignee: Althea Technologies, Inc., San Diego, CA (US)

( * ) Notice: Subject to any disclaimer, the term of this patent is extended or adjusted under 35 U.S.C. 154(b) by 0 days.

(21) Appl. No.: 09/771,372

(22) Filed: Jan. 27, 2001

(65) Prior Publication Data

US 2002/0160361 A1 Oct. 31, 2002

Related U.S. Application Data

(60) Provisional application No. 60/179,006, filed on Jan. 28, 2000.

(51) Int. Cl.[7] .................. G06F 19/00; C12P 19/30; C12Q 1/68

(52) U.S. Cl. .................. 702/20; 435/6; 435/91.2; 536/24.33

(58) Field of Search .................. 435/6, 91.2; 702/20; 356/320, 328, 344; 536/24.33, 25.3; 706/13

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,883,750 A | 11/1989 | Whiteley et al. |
| 5,143,854 A | 9/1992 | Pirrung et al. |
| 5,296,375 A | 3/1994 | Kricka et al. |
| 5,304,487 A | 4/1994 | Wilding et al. |
| 5,599,672 A | 2/1997 | Liang et al. |
| 5,691,141 A | 11/1997 | Koster |
| 5,700,642 A | 12/1997 | Monforte et al. |
| 5,714,320 A | 2/1998 | Kool |
| 5,807,522 A | 9/1998 | Brown et al. |
| 5,854,033 A | 12/1998 | Lizardi |
| 5,856,174 A | 1/1999 | Lipshutz et al. |
| 5,866,330 A | 2/1999 | Kinzler et al. |
| 5,876,978 A | 3/1999 | Willey et al. |
| 5,882,856 A | 3/1999 | Shuber |
| 6,027,889 A | 2/2000 | Barany et al. |
| 6,074,831 A | 6/2000 | Yakhini et al. |
| 6,090,558 A | 7/2000 | Butler et al. |
| 6,104,028 A | 8/2000 | Hunter et al. |
| 6,124,092 A | 9/2000 | O'Neil et al. |
| 6,132,685 A | 10/2000 | Kercso et al. |
| 6,136,535 A | 10/2000 | Lorincz et al. |
| 6,140,054 A | 10/2000 | Wittwer et al. |

FOREIGN PATENT DOCUMENTS

| | | |
|---|---|---|
| EP | 320308 A2 | 6/1989 |
| WO | WO 94/05414 A1 | 3/1994 |
| WO | WO 96/37630 A1 | 11/1996 |
| WO | WO 96/41012 | 12/1996 |
| WO | WO 97/27327 A2 | 7/1997 |
| WO | WO 98/36095 A1 | 8/1998 |

OTHER PUBLICATIONS

Liang et al. (1992) "Differential Display of Eukarotic Messenger RNA by Means of the Polymerase Chain Reaction." *Science* 257:967–971.

Livak et al. (1995) "Oligonucleotides with Fluorescent Dyes at Opposite Ends Provide a Quenched Probe System Useful for Detecting PCR Product and Nucleic Acid Hybridization." *PCR Methods Applications* 4:357–362.

Mazumder et al. (1998) A high throughput method to investigate oilgodeoxyribonucleotide hybridization kinetics and thermodynamics. *Nucleic Acids Research* 26(8):1996–2000.

Mehta et al. (1999) Bridge–Overlap–Extension PCR Methods for Constructing Chimeric Genes. *Bio Techniques* 26(6):1082–1086.

Sagerstorm et al. (1997) "Substractive Cloning: Past, Present and Future." *Annual Rev. Biochem.* 66:751–783.

Schena et al. (1995) "Quantitative Monitoring of Gene Expression Patterns with a Complementary DNA Microarray." *Science* 270:467–470.

Su et al. (1997) "High–Throughput RT–PCR Analysis of Multiple Transcripts Using a Microplate RNA Isolation Procedure." *BioTechniques* 22:1107–1113.

Velculescu et al. (1995) "Serial Analysis of Gene Expression." *Science* 270:484–487.

Walker et al., (1992) "Strand displacement amplification—an isothermal, in vitro DNA amplification technique." *Nucleic Acids Research* 20(7):1691–1696.

Wang et al. (1989) "Quantitation of mRNA by the polymerase chain reaction" *Proc. Natl. Acad. Sci. USA* 86:9717–9721.

Welsh et al. (1992) Arbitrarily primed PCR fingerprinting of RNA. *Nucleic Acids Research* 20(19):4965–4970.

(List continued on next page.)

*Primary Examiner*—Marjorie Moran
(74) *Attorney, Agent, or Firm*—Angela P. Horne; Quine Intellectual Property Law Group, P.C.

(57) ABSTRACT

This invention provides methods, compositions and kits for gene expression analysis and gene expression profiling. The methods of the invention are highly sensitive; have a wide dynamic range; are rapid and inexpensive; have a high throughput; and allow the simultaneous differential analysis of a defined set of genes. The methods, compositions and kits of the invention also provide tools for gene expression data collection and relational data analysis.

82 Claims, 5 Drawing Sheets

OTHER PUBLICATIONS

Figure 1:
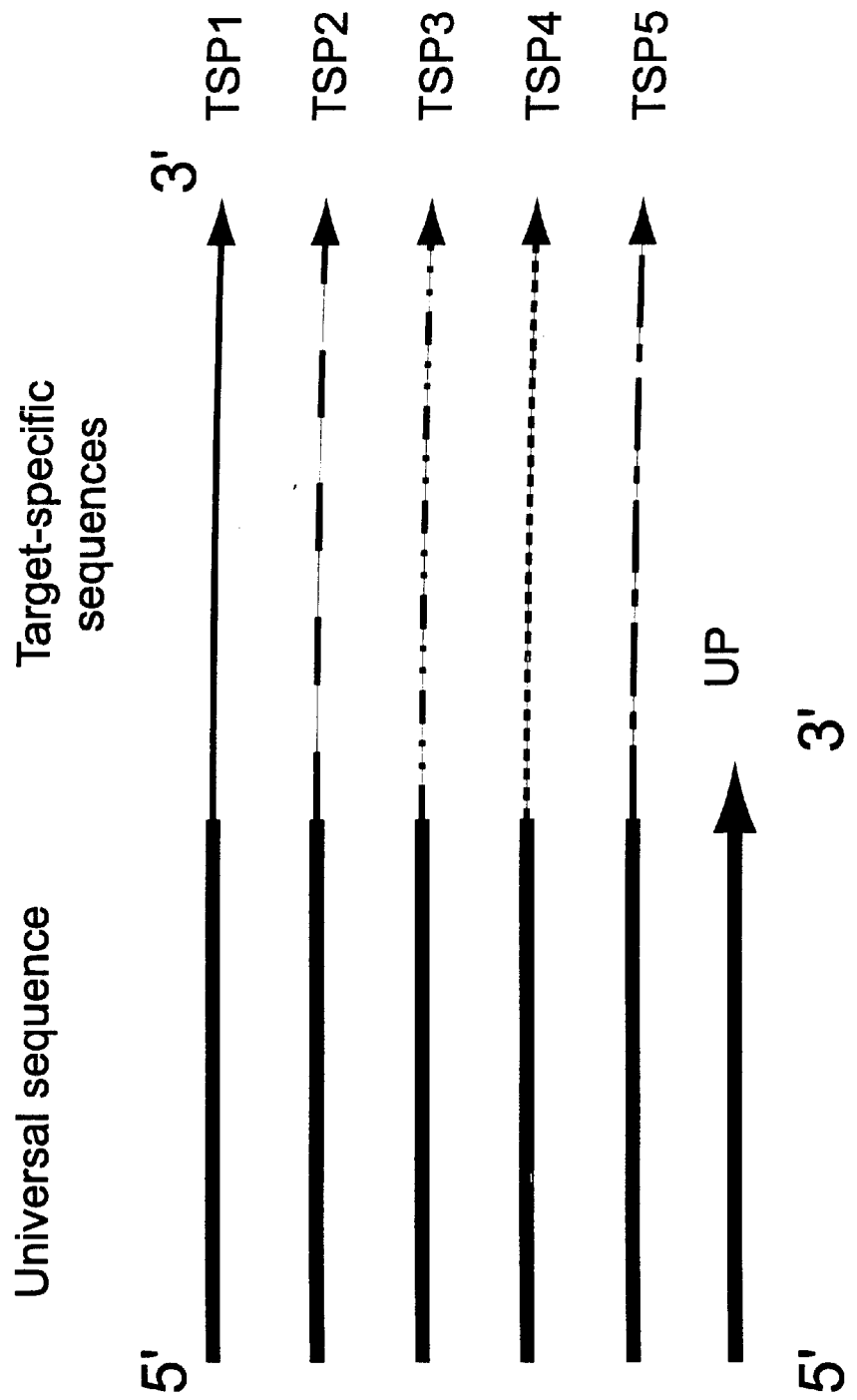

Woolley et al. (1994) "Ultra–high–speed DNA fragment separations using microfabricated capillary array electrophoresis chips." *Proc. Natl. Acad. Sci. USA* 91:11348–11352.

Wu et al. (1993) Matrix–assisted Laser Desorption Time–of–flight Mass Spectrometry of Oligonucleotides Using 3–Hydroxypicolinic Acid as an Ultraviolet–sensitive Matrix. *Rapid Communications in Mass Spectrometry* 7: 142–146.

Zang et al. (1997) "Gene Expression Profiles in Normal and Cancer Cells." *Science* 276: 1268–1272.

Adams et al. (1991)"Complementary DNA Sequencing: Expressed Sequence Tags and Human Genome Project." *Science* 252:1651–1656.

Alivisatos et al. (1996) "Organization of 'nanocrystal molecules' using DNA" *Nature* 382:609–611.

Becker–Andre et al. (1989) Absolute mRNA quantification using the Polymerase chain reaction (PCR). A novel approach by a PCR aided transcript titration assay (PATTY). *Nucleic Acids Research* 17:9437–9446.

Fodor et al. (1991) "Light–Directed, Spatially Addressable Parallel Chemical Synthesis." *Science* 251:767–773.

Frohman (1988) "Rapid production of full–length cDNAs from rare transcripts: Amplification using a single gene–specific oligonucleotide primer." *Proc. Natl. Acad. Sci. USA* 85: 8998–9002.

Gaus et al. (1993) Quantitative analysis of lymphokine mRNA expression by a nonradioactive method usig PCR and anion exchange chromatography. *Journal of Immunological Methods* 158: 229–239.

Gilliland et al. (1990) "Analysis fo cytokine mRNA and DNA: Detection and quantitation by completitive polymerase chain reaction." *Proc. Natl. Acad. Sci. USA* 87:2725–2729.

Griffin et al. (1999) "Direct genetic analysis by matrix–assisted laser desorption/ionization mass spectrometry." *Proc. Natl. Acad. Sci. USA* 96: 6301–6306.

Guatelli et al. (1990) "Isothermal, in vitro amplificaiton of nucleic acids by a multienzyme reaction modeled after retroviral replication." *Proc. Natl. Acad. Sci. USA* 87:1874–1878.

Kasianowicz et al. (1996) "Characterization of individual polynucleotide molecules using a membrane channel." *Proc. Natl. Acad. Sci. USA* 93: 13770–13773.

Katz et al. (1990) Rapid Analysis and Purification of Polymerase Chain Reaction Products by High–Performance Liquid Chromatography. *BioTechniques* 8(5): 546–555.

Kievits et al. (1991) "NASBA™ isothermal enzymatic in vitro nucleic acid amplification optimized for the diagnosis of HIV–1 infection" *Journal of Virological Methods* 35(3):273–286.

Kwoh et al. (1989) "Transcription–based amplification system and detection of amplified human immunodeficiency virus type 1 with a bead–based sandwich hybridization format." *Proc. Natl. Acad. Sci. USA* 86(4): 1173–1177.

Li et al. (1999) Single nucleotide polymorphism determination using primer extension and time–of–flight mass spectrometry. *Electrophoresis* 20:1258–1265.

METHODS FOR ANALYSIS OF GENE EXPRESSION

CROSS-REFERENCES TO RELATED APPLICATIONS

This application claims benefit of U.S. application No. 60/179,006, filed Jan. 28, 2000, the full disclosure of which is incorporated herein by reference.

STATEMENT AS TO RIGHTS TO INVENTIONS MADE UNDER FEDERALLY SPONSORED RESEARCH AND DEVELOPMENT

The United States government may own rights in the present invention pursuant to grant numbers HG01700-02, R43-CA83382 and N43-ES-81006 from the National Institutes of Health.

BACKGROUND OF THE INVENTION

Functional genomics is a rapidly growing area of investigation, which includes research into genetic regulation and expression, analysis of mutations that cause changes in gene function, and development of experimental and computational methods for nucleic acid and protein analyses. The Human Genome Project has been the major catalyst driving this research; it has been through the development of high-throughput technologies that it has been possible to map and sequence complex genomes. However, while the nucleic acid sequence information elicited by these technologies represents the "structural" aspects of the genome, it is the interworkings of the genes encoded therein, and the gene products derived from these sequences, that will give a meaningful context to this information. In particular, gene expression monitoring can be utilized to examine groups of related genes, interlocking biochemical pathways, and biological networks as a whole.

This rapidly growing set of cloned human genes provides a plethora of candidate drug targets for testing against complex chemical libraries. In order to efficiently test the impact(s) of a large number of putative drug compounds on the expression profile of one or more sets of genes, methods are needed that are sensitive, quantitative, extremely rapid, and adaptable to automation, in order to be cost-effective. Present day technologies do not meet these demands. The present invention addresses this need by providing novel methods for analyzing gene expression, systems for implementing these techniques, compositions for preparing a plurality of amplification products from a plurality of mRNA target sequences, and related pools of amplification products.

SUMMARY OF THE INVENTION

The present invention provides methods for analyzing gene expression. The methods include obtaining a plurality of cDNA target sequences, and multiplex amplifying these sequences, a process which involves combining the plurality of target sequences with a plurality of target-specific primers and one or more universal primers, to produce a plurality of amplification products. The target sequences are obtained in any of a number of manners, such as by performing reverse transcription on a set of mRNA molecules. The mRNA molecules are optionally derived from cells, organisms, or cell cultures, which are optionally exposed to one or more specific treatments that potentially alter the biological state of the cell, organism, or cell culture.

Target-specific primers for use in the methods of the present invention include oligonucleotides comprising a first sequence that is derived from a target gene of interest and positioned within a 3' region of the oligonucleotide, and a second sequence that is complementary to a universal primer and positioned within the 5' region of the oligonucleotide. The target specific primers can be categorized as forward primers or reverse primers, depending upon the relative orientation whether the primer versus the polarity of the nucleic acid sequence (e.g., whether the primer binds to the coding strand or a complementary (noncoding) strand of the target sequence).

The universal primers used in the methods of the present invention are sequences common to a plurality of target-specific primers, but preferably not present in the template nucleic acid (i.e., the plurality of target sequences). As such, a universal primer typically does not hybridize to the target sequence template during a PCR reaction. However, since the universal primer sequence is complementary to a portion of one or more target-specific primers used in the present invention, the universal primer can initiate polymerization using a target-specific primer-amplified product as a template. In some embodiments of the present invention, multiple universal primers having sequences distinct from one another are utilized; these universal primers are then called "semi-universal" primers. As one example, a plurality of semi-universal primers can include primer sequences that are complementary to one or more forward target-specific primers, one or more reverse target-specific primers, or a combination thereof.

Optionally, the multiplex amplification process involves simultaneously amplifying a plurality of cDNA molecules in the same reaction mixture. This can be achieved, for example, by employing one or more target-specific primer pairs (where each pair comprising a forward target-specific primer and a reverse target-specific primer) and one or more universal primer pairs, (also comprising pairs of forward and reverse universal primers). In some embodiments of the present invention, the multiplex amplification involves providing the universal primer in an excess concentration relative to the target-specific primer.

In some embodiments of the methods of the present invention, the length of one or more of the universal primers or target-specific primers is altered prior to combination in the multiplex amplification step. This alteration in length can be achieved, e.g., by adding nucleotides to the end of the primer sequence, inserting nucleotides within the primer sequence, incorporating a non-nucleotide linker within the primer sequence, or cleaving a cleavable linkage within the primer sequence. As one example, alteration of the length of a target-specific primer is achieved by inserting nucleotides between the universal sequence portion (i.e., that sequence complementary to the universal primer sequence) and the target-specific sequence of the primer.

One or more of the nucleic acid sequences used as universal primers and target-specific primers in the methods of the present invention can optionally include a cleavable linkage or a non-nucleotide linker as a sequence element. This non-nucleotide linker can include, e.g., non-cleavable linkages, alkyl chains, or abasic nucleotides. Furthermore, the nucleic acid sequences used as universal primers and target-specific primers in the methods of the present invention can optionally include one or more labels. Labels for use in the methods of the present invention can include, e.g., a chromaphore, a fluorophore, a dye, a releasable label, a mass label, an affinity label, a friction moiety, a hydrophobic group, an isotopic label, or a combination thereof. The same label can be incorporated into disparate primers used in a multiplexed amplification; alternatively, unique labels or combination of labels can be associated with each member of the plurality of primers.

Furthermore, the multiplex amplification optionally includes a reference sequence that contains a region homologous to at least one member of the plurality of target-specific primers. The reference sequence (or sequences) can be endogenously present in the cDNA containing the target sequence, or it can be exogenously added to the cDNA sample.

One or more members of the plurality of amplification products are separated by any of a variety of techniques known to those of skill in the art. In a preferred embodiment of the present invention, the members are separated using one or more separation techniques, such as mass spectrometry, electrophoresis (using, for example, capillary electrophoresis, microcapillary electrophoresis, agarose and/or acrylamide gel platforms), chromatography (e.g., such as HPLC or FPLC), or various microfluidic techniques.

The one or more members are detected by any of a number of techniques, thereby generating one or more sets of gene expression data. For example, in a preferred embodiment, the amplification products are separated and detected by performing HPLC followed by mass spectroscopy.

Detection is performed, for example, by measuring the presence, absence, or quantity/amplitude of one or more properties of the amplification products. Example properties of the amplification products include, but are not limited to, mass, light absorption or emission, and one or more electrochemical properties. In embodiments in which one or more of the primers includes a label, the inherent property can be dependent upon the identity of the label. In one embodiment, detection of the amplification products involves resolving a first signal from a singly labeled amplification product and a second signal from a single labeled (or multiply labeled) amplification product by deconvolution of the data. In an alternative embodiment, detection of the amplification products involves resolving a first signal from a singly labeled amplification product and a second signal from a single or multiply labeled amplification product by reciprocal subtraction of the first or second signal from an overlapping signal. Thus, one or more amplification products are detected and the information collected is used to generate a set of gene expression data.

The set of gene expression data are stored in a database; this data is then used, e.g., to perform a comparative analysis (for example, by measuring a ratio of each target gene to each reference gene or other analysis of interest).

The present invention also provides methods for analyzing gene expression including the steps of obtaining cDNA from a plurality of samples for a plurality of target sequences; performing a plurality of multiplexed amplifications of the target sequences, thereby producing a plurality of multiplexed amplification products; pooling the plurality of multiplexed amplification products; separating the plurality of multiplexed amplification products; detecting the plurality of multiplexed amplification products, thereby generating a set of gene expression data; storing the set of gene expression data in a database; and performing a comparative analysis of the set of gene expression data. As in the previous embodiments, a plurality of target-specific primers and universal primers are employed in the multiplexed amplification step. Either the universal primer(s) or the target-specific primer(s) can be labeled. In one embodiment of these methods, a first multiplexed amplification is performed using a primer having a first label that produces a first signal, and a second multiplexed amplification is performed with a primer comprising a second label that produces a second signal, wherein the first and second signals are distinguishable from one another.

In another embodiment, the plurality of amplification products are detected by shifting the mobility of member amplification products relative to one another For example, amplification of the target sequences is performed using universal primers having two or more lengths; detection of the plurality of multiplexed amplification products produced using these primers involves measuring one or more size shifts among the plurality of multiplexed amplification products. Alternatively, the method is performed using target-specific primers having two or more lengths, leading to generation of differentially-sized amplification products. The shift in size can be achieved, for example, by using primers having cleavable linkages incorporated into their sequences. Alternatively, the shift in size can be achieved by incorporation of a friction moiety into one or more of the universal primers, thereby creating a reduction in mobility of the amplification products.

The multiplex amplification reaction used in the methods of the present invention includes, but is not limited to, a polymerase chain reaction, a transcription-based amplification, a self-sustained sequence replication, a nucleic acid sequence based amplification, a ligase chain reaction, a ligase detection reaction, a strand displacement amplification, a repair chain reaction, a cyclic probe reaction, a rapid amplification of cDNA ends, an invader assay, a bridge amplification or rolling circle amplification, or a combination thereof.

The present invention also provides methods for analyzing gene expression including the steps of obtaining cDNA from multiple samples; amplifying a plurality of target sequences from the cDNA, thereby producing a multiplex of amplification products; separating and detecting the amplification products using a high throughput platform, wherein detecting generates a set of gene expression data; storing the set of gene expression data in a database; and performing a comparative analysis of the set of gene expression data.

The methods of the present invention optionally include performing one or more of the amplifying, separating or detecting steps in a high throughput format. For example, the reactions can be performed in multi-well plates. Optionally, anywhere between about 96 and about 5000 reactions, preferably between about 500 and 2000 reactions, and more preferably about 1000 reactions, are performed per hour using the methods of the present invention. Furthermore, one or more miniaturized scale platforms can be used to perform the methods of the present invention.

The present invention also provides systems for analyzing gene expression. The elements of the system include, but are not limited to, a) an amplification module for producing a plurality of amplification products from a pool of target sequences; b) a detection module for detecting one or more members of the plurality of amplification products and generating a set of gene expression data comprising a plurality of data points; and c) an analyzing module in operational communication with the detection module, the analyzing module comprising a computer or computer-readable medium comprising one or more logical instructions which organize the plurality of data points into a database and one or more logical instructions which analyze the plurality of data points. Any or all of these modules can comprise high throughput technologies and/or systems.

The amplification module of the present invention includes at least one pair of universal primers and at least one pair of target-specific primers for use in the amplification process. Optionally, the amplification module includes a unique pair of universal primers for each target sequence. Furthermore, the amplification module can include components to perform one or more of the following reactions: a polymerase chain reaction, a transcription-based amplification, a self-sustained sequence replication, a nucleic acid sequence based amplification, a ligase chain reaction, a ligase detection reaction, a strand displacement amplification, a repair chain reaction, a cyclic probe reaction, a rapid amplification of cDNA ends, an invader assay, or various solution phase and/or solid phase assays (for example, bridge amplification or rolling circle amplification). The detection module can include systems for implementing separation of the amplification products; exemplary detection modules include, but are not limited to, mass spectrometry instrumentation and electrophoretic devices.

The analyzing module of the system includes one or more logical instructions for analyzing the plurality of data points generated by the detection system. For example, the instructions can include software for performing difference analysis upon the plurality of data points. Additionally (or alternatively), the instructions can include or be embodied in software for generating a graphical representation of the plurality of data points. Optionally, the instructions can be embodied in system software which performs combinatorial analysis on the plurality of data points.

The present invention also provides kits for obtaining a multiplex set of amplification products of target genes and references-genes. The kits of the present invention include a) at least one pair of universal primers; b) at least one pair of target-specific primers; c) at least one pair of reference gene-specific primers; and d) one or more amplification reaction enzymes, reagents, or buffers. The kits optionally further include software for storing and analyzing data obtained from the amplification reactions.

Additionally, the present invention provides compositions for preparing a plurality of amplification products from a plurality of mRNA target sequences. The compositions include one or more pairs of universal primers; and one or more pairs of target-specific primers. The present invention also provides for the use of the kits of the present invention for practicing any of the methods of the present invention, as well as the use of a composition or kit as provided by the present invention for practicing a method of the present invention. Furthermore, the present invention provides assays utilizing any of these uses.

BRIEF DESCRIPTION ON THE FIGURES

The following drawings form part of the present specification and are included to further demonstrate certain aspects of the present invention. The invention may be better understood by reference to one or more of these drawings in combination with the detailed description of specific embodiments presented herein.

FIG. 1: Schematic of one embodiment of a set of target-specific primers and a universal primer employed in the present invention. The abbreviation "TSP" indicates a target-specific primer, while "UP" indicates a universal primer. Different line patterns (bold, dashed, etc.) symbolize different DNA sequences.

Figure 2:
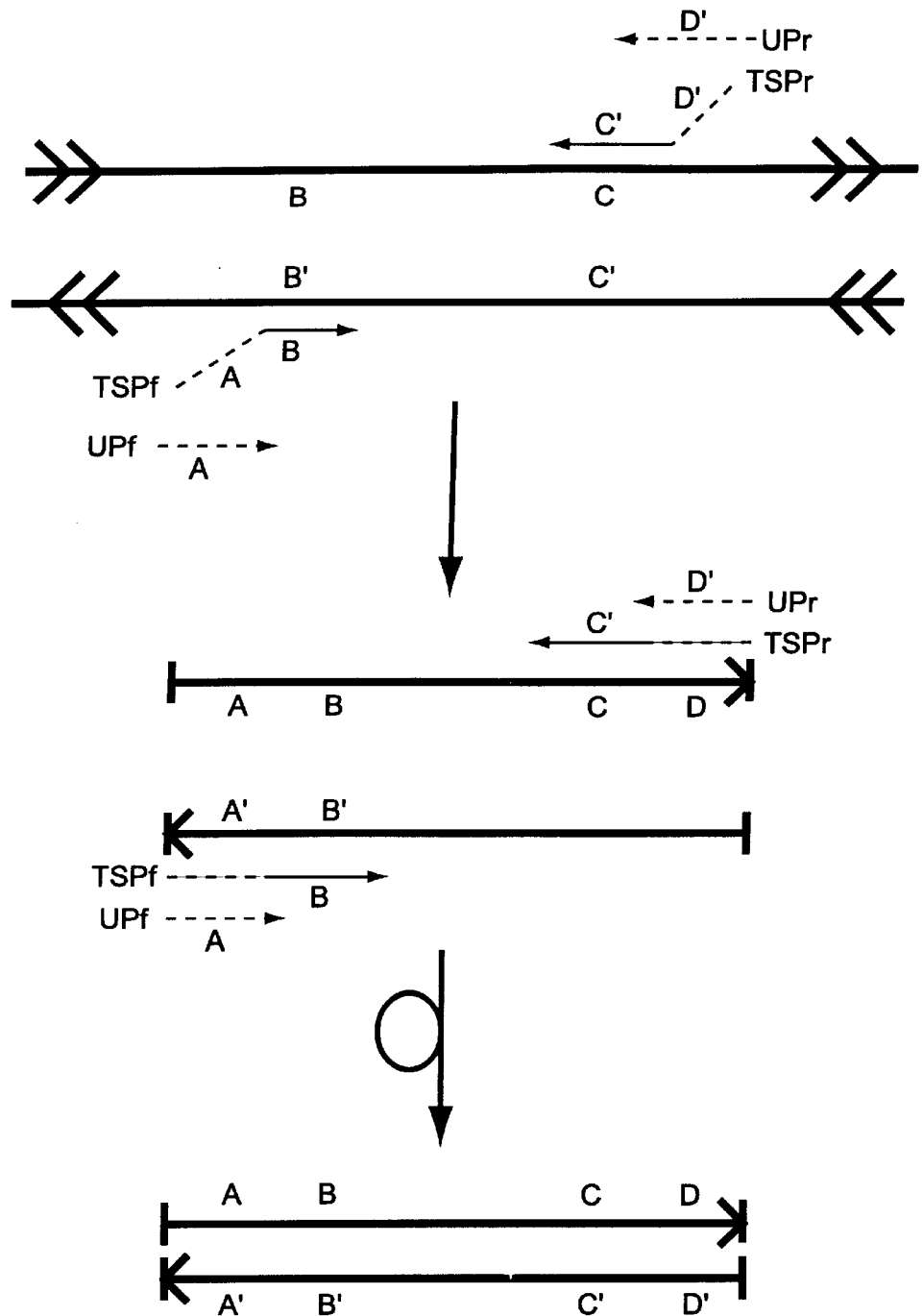

FIG. 2: Schematic drawing depicting coupled target-specific and universal priming of a PCR reaction.

Figure 3:
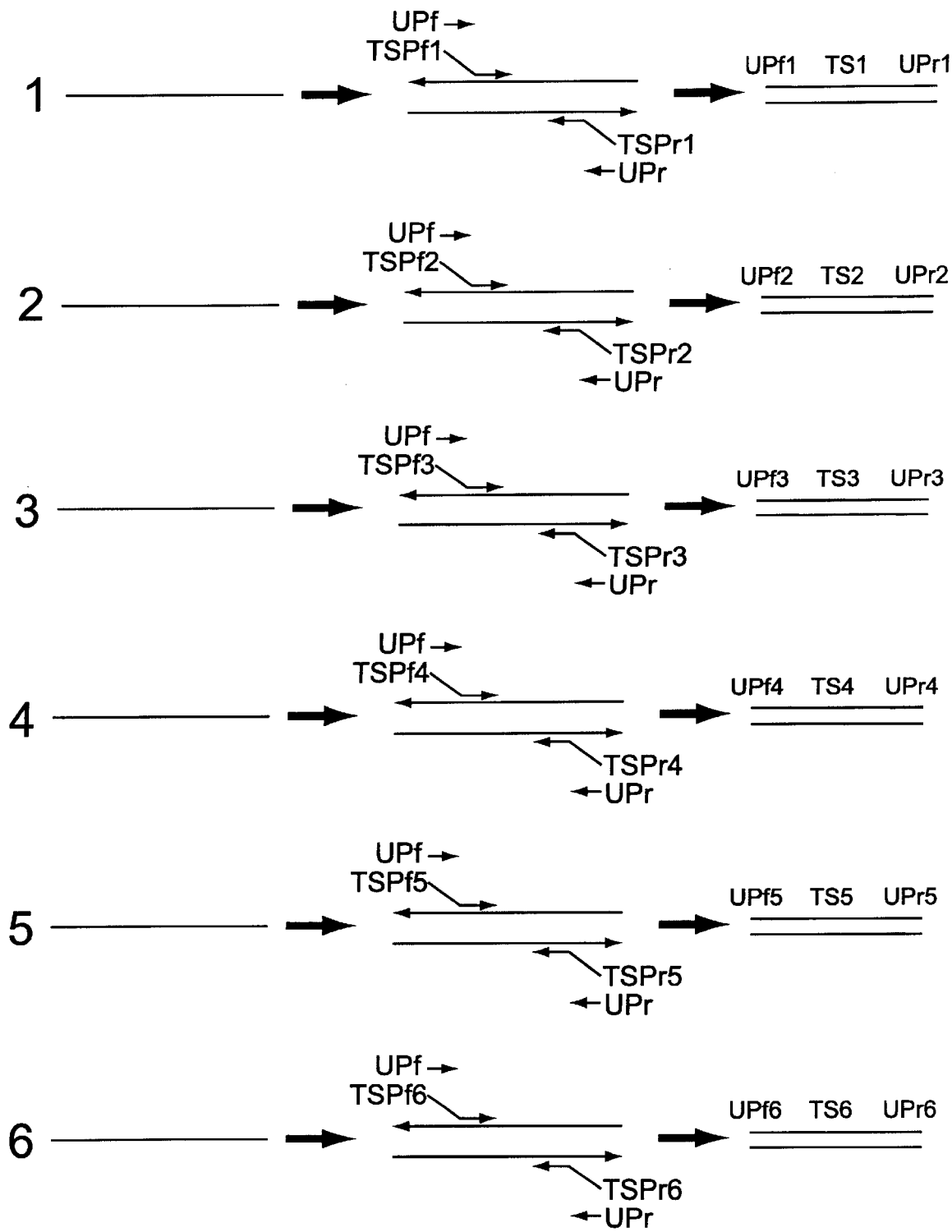

FIG. 3: Schematic depiction of exemplary reactions occurring in a multiplexed reverse transcriptase-based polymerase chain reaction (RT-PCR) reaction, using a combination of target-specific and universal primers.

Figure 4:
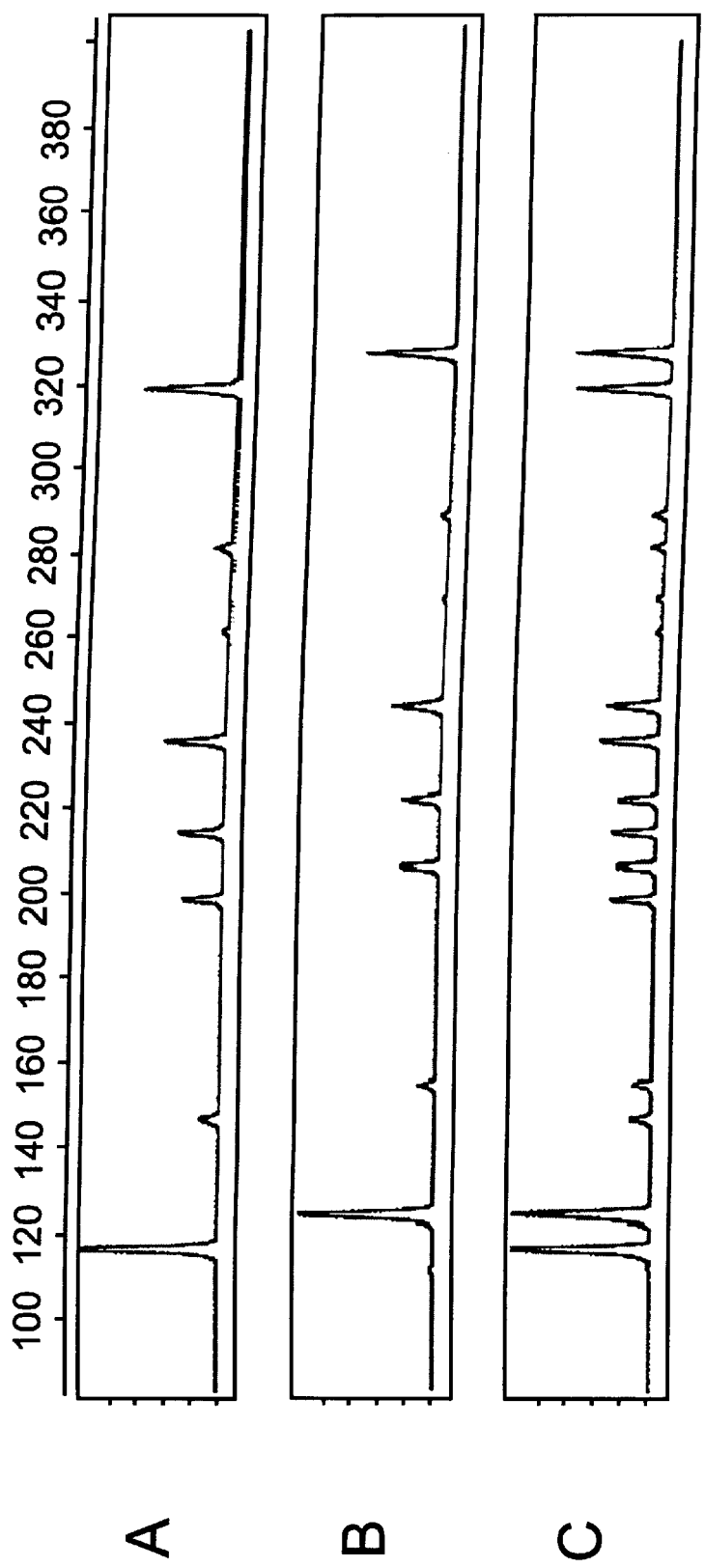

FIG. 4: Exemplary profiles of original and "shifted" multiplex gene sets.

Figure 5:
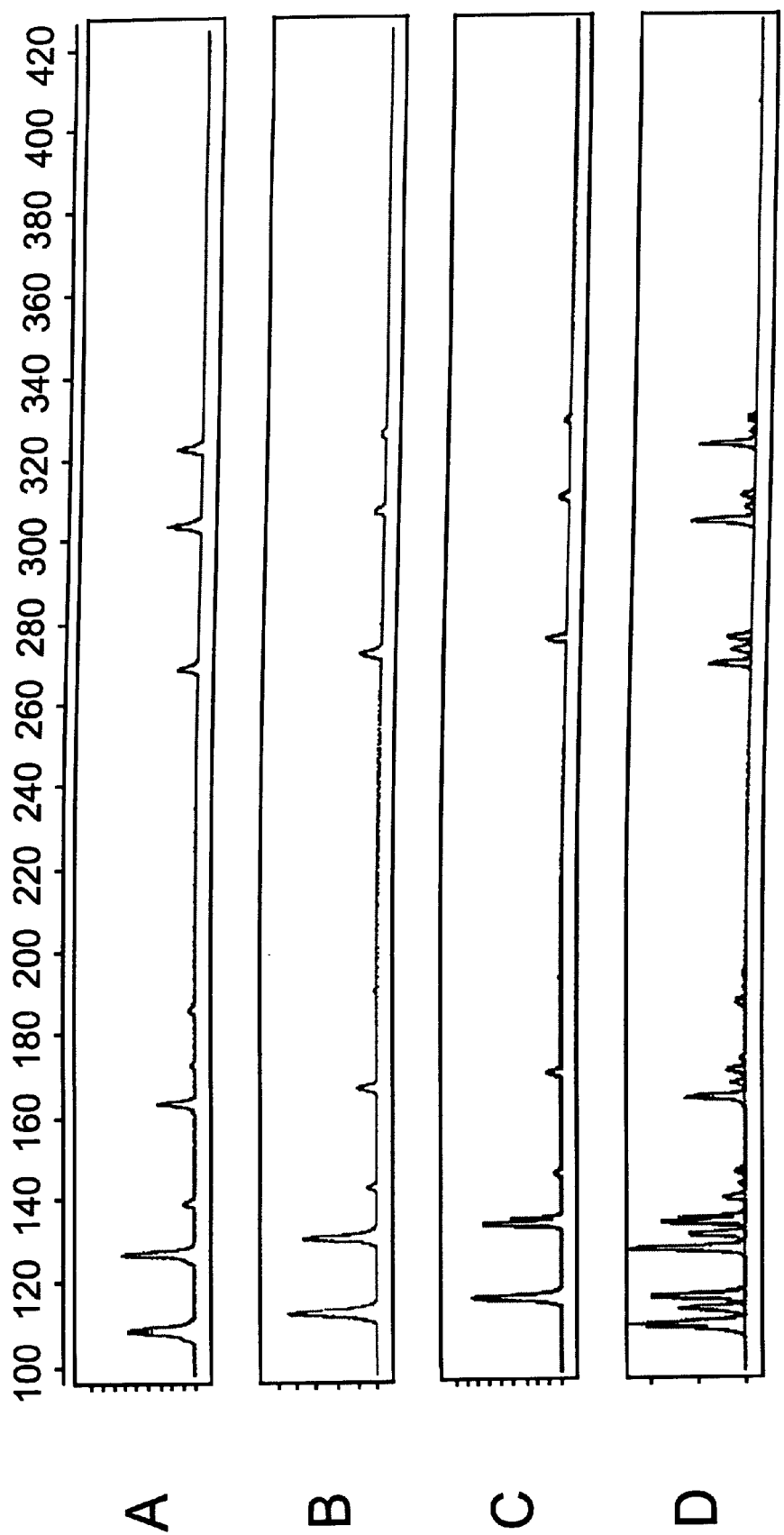

FIG. 5: Exemplary profiles of multiplex gene sets using multiple fluorescent dye labels.

DETAILED DISCUSSION

Definitions

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a device" includes a combination of two or more such devices, reference to "a gene fusion construct" includes mixtures of constructs, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, currently preferred materials and methods are described herein.

In describing and claiming the present invention, the following terminology will be used in accordance with the definitions set out below.

The term "absolute abundance" or "absolute gene expression levels" refers to the amount of a particular species (e.g., gene expression product) present in a sample.

The term "amplified product" refers to a nucleic acid generated by any method of nucleic acid amplification.

The term "attenuation" refers to a method of reducing the signal intensities of extremely abundant reaction products in a multiplex, such that the signals from all products of a multiplex set of products fall within the dynamic range of the detection platform used for the assay.

The term "blocking group" refers to a chemical modification at the 3' end of an amplification primer that does not interfere with hybridization between the primer and its target sequence, but cannot be extended by a DNA polymerase.

The term "cDNA" refers to complementary or "copy" DNA. Generally cDNA is synthesized by a DNA polymerase using any type of RNA molecule (e.g., typically mRNA) as a template. Alternatively, the cDNA can be obtained by directed chemical syntheses.

The term "chemical treatment" refers to the process of exposing a cell, cell line, tissue or organism to a chemical or biochemical compound (or library of compounds) that has/have the potential to alter its gene expression profile.

The term "complementary" refers to nucleic acid sequences capable of base-pairing according to the standard Watson-Crick complementary rules, or being capable of hybridizing to a particular nucleic acid segment under relatively stringent conditions. Nucleic acid polymers are optionally complementary across only portions of their entire sequences.

The term "environmental stress" refers to an externally applied factor or condition that may cause an alteration in the gene expression profile of a cell.

The term "friction group" refers to a chemical or physical moiety attached to a nucleic acid for the purposes of reducing the mobility by frictional drag of that nucleic acid in a matrix or fluid across which an electric field is applied.

The term "gene" refers to a nucleic acid sequence encoding a gene product. The gene optionally comprises sequence information required for expression of the gene (e.g., promoters, enhancers, etc.).

The term "gene expression" refers to transcription of a gene into an RNA product, and optionally to translation into one or more polypeptide sequences.

The term "gene expression data" refers to one or more sets of data that contain information regarding different aspects of gene expression. The data set optionally includes information regarding: the presence of target-transcripts in cell or cell-derived samples; the relative and absolute abundance levels of target transcripts; the ability of various treatments to induce expression of specific genes; and the ability of various treatments to change expression of specific genes to different levels.

The term "high throughput format" refers to analyzing more than about 10 samples per hour, preferably about 50 or more samples per hour, more preferably about 100 or more samples per hour, most preferably about 250, about 500, about 1000 or more samples per hour.

The term "hybridization" refers to duplex formation between two or more polynucleotides, e.g., to form a double-stranded nucleic acid. The ability of two regions of complementarity to hybridize and remain together depends of the length and continuity of the complementary regions, and the stringency of hybridization conditions.

The term "label" refers to any detectable moiety. A label may be used to distinguish a particular nucleic acid from others that are unlabeled, or labeled differently, or the label may be used to enhance detection.

The terms "microplate," "culture plate," and "multiwell plate" interchangeably refer to a surface having multiple chambers, receptacles or containers and generally used to perform a large number of discreet reactions simultaneously.

The term "miniaturized format" refers to procedures or methods conducted at submicroliter volumes, including on both microfluidic and nanofluidic platforms.

The term "multiplex reaction" refers to a plurality of reactions conducted simultaneously in a single reaction mixture.

The term "multiplex amplification" refers to a plurality of amplification reactions conducted simultaneously in a single reaction mixture.

The term "nucleic acid" refers to a polymer of ribonucleic acids or deoxyribonucleic acids, including RNA, mRNA, rRNA, tRNA, small nuclear RNAs, cDNA, DNA, PNA, or RNA/DNA copolymers. Nucleic acid may be obtained from a cellular extract, genomic or extragenomic DNA, viral RNA or DNA, or artificially/chemically synthesized molecules.

The term "platform" refers to the instrumentation method used for sample preparation, amplification, product separation, product detection, or analysis of data obtained from samples.

The term "primer" refers to any nucleic acid that is capable of hybridizing at its 3' end to a complementary nucleic acid molecule, and that provides a free 3' hydroxyl terminus which can be extended by a nucleic acid polymerase.

The term "reference sequence" refers to a nucleic acid sequence serving as a target of amplification in a sample that provides a control for the assay. The reference may be internal (or endogenous) to the sample source, or it may be an externally added (or exogenous) to the sample. An external reference may be either RNA, added to the sample prior to reverse transcription, or DNA (e.g., cDNA), added prior to PCR amplification.

The term "relative abundance" or "relative gene expression levels" refers to the abundance of a given species relative to that of a second species. Optionally, the second species is a reference sequence.

The term "RNA" refers to a polymer of ribonucleic acids, including RNA, mRNA, rRNA, tRNA, and small nuclear RNAs, as well as to RNAs that comprise ribonucleotide analogues to natural ribonucleic acid residues, such as 2-O-methylated residues.

The term "semi-universal primer" refers to a primer that is capable of hybridizing with more than one, but not all, of the target-specific primers in a multiplexed reaction.

The term "separation system" refers to any of a set of methodologies that can be employed to effect a size separation of the products of a reaction.

The term "size separation" refers to physical separation of a complex mixture of species into individual components according to the size of each species.

The term "target," "target sequence," or "target gene sequence" refers to a specific nucleic acid sequence, the presence, absence or abundance of which is to be determined. In a preferred embodiment of the invention, it is a unique sequence within the mRNA of an expressed gene.

The term "target-specific primer" refers to a primer capable of hybridizing with its corresponding target sequence. Under appropriate conditions, the hybridized primer can prime the replication of the target sequence.

The term "template" refers to any nucleic acid polymer that can serve as a sequence that can be copied into a complementary sequence by the action of, for example, a polymerase enzyme.

The term "transcription" refers to the process of copying a DNA sequence of a gene into an RNA product, generally conducted by a DNA-directed RNA polymerase using the DNA as a template.

The term "treatment" refers to the process of subjecting one or more cells, cell lines, tissues, or organisms to a condition, substance, or agent (or combinations thereof) that may cause the cell, cell line, tissue or organism to alter its gene expression profile. A treatment may include a range of chemical concentrations and exposure times, and replicate samples may be generated.

The term "universal primer" refers to a replication primer comprising a universal sequence.

The term "universal sequence" refers to a sequence contained in a plurality of primers, but preferably not in a complement to the original template nucleic acid (e.g., the target sequence), such that a primer composed entirely of universal sequence is not capable of hybridizing with the template.

Gene Expression as a Measure of the Biological State of a Cell

Transcription of genes into RNA is a critical early step in gene expression. Consequently, the coordinated activation or suppression of transcription of particular genes is an important component of the overall regulation of expression. A variety of well-developed techniques have been established that provide ways to analyze and quantitate gene transcription.

Some of the earliest methods are based on detection of a label in RNA hybrids or protection of RNA from enzymatic degradation (see, for example, Current Protocols in Molecular Biology, F. M. Ausubel et al., eds., Current Protocols, a joint venture between Greene Publishing Associates, Inc. and John Wiley & Sons, Inc., supplemented through 1999). Methods based on detecting hybrids include northern blots and slot/dot blots. These two techniques differ in that the components of the sample being analyzed are resolved by size in a northern blot prior to detection, which enables identification of more than one species simultaneously. Slot blots are generally carried out using unresolved mixtures or sequences, but can be easily performed in serial dilution, enabling a more quantitative analysis. Both techniques are very time-consuming and require a fair amount of manual manipulation, making them expensive and unsuitable for high throughput applications.

In situ hybridization is a technique that monitors transcription by directly visualizing RNA hybrids in the context of a whole cell. This method provides information regarding subcellular localization of transcripts. However, it is not very quantitative, and is extremely technically demanding and time-consuming. As a consequence, this technique is best suited for basic research applications.

Techniques to monitor RNA that make use of protection from enzymatic degradation include S1 analysis and RNAse protection assays (RPAs). Both of these assays employ a labeled nucleic acid probe, which is hybridized to the RNA species being analyzed, followed by enzymatic degradation of single-stranded regions of the probe. Analysis of the amount and length of probe protected from degradation is used to determine the quantity and endpoints of the transcripts being studied. Although both methods can yield quantitative results, they are time-consuming and cumbersome, making them poor candidates for a high-throughput, low cost general assay for gene expression.

A second family of assays developed for monitoring transcription makes use of cDNA derived from mRNA. Because the material analyzed is DNA, these assays are less sensitive to degradation, and also provide partial and/or full clones with which to localize and clone genes or coding sequences of interest. Methods include sequencing cDNA inserts of an expressed sequence tag (EST) clone library (Adams et al. (1991) Science 252:1651–1656), which may be coupled with subtractive hybridization to improve sensitivity (Sagerstrom et al. (1997) Annul Rev. Biochem. 66:751–783), and serial analysis of gene expression ("SAGE", described in U.S. Pat. No. 5,866,330 to Kinzler et al.; Velculescu et al. (1995) Science 270:484–487); and Zhang et al. (1997) Science 276:1268–1272). Both of these methods have been useful for identification of novel, differentially expressed genes. However, their methodologies yield untargeted information, i.e., they survey the whole spectrum of mRNA in a sample rather than focusing on a predetermined set. As a result, very large data sets are required to derive reliable quantitative data, making these methods inappropriate and far too costly for high throughput screening strategies.

Reverse transcriptase-mediated PCR (RT-PCR) gene expression assays are directed at specified target gene products, overcoming some of the shortcomings described above. These assays are derivatives of PCR in which amplification is preceded by reverse transcription of mRNA into cDNA. Because the mRNA is amplified, this type of assay can detect transcripts of very low abundance; however, the assay is not quantitative. Adaptations of this assay, called competitive RT-PCR (Becker-Andre and Hahlbrock (1989) Nucleic Acids Res. 17:9437–9446; Wang et al. (1989) Proc. Natl. Acad. Sci. USA 86:9717–9721; Gilliland et al. (1990) Proc. Natl. Acad. Sci. USA 87:2725–2729) have been developed that are more quantitative. In these assays, a known amount of exogenous template is added to the reaction mixture, to compete with the target for amplification. The exogenous competitor is titrated against the target, allowing for quantitation of a specified cDNA in the sample by comparing the amplification of both templates within the same reaction mixture. Because titration is required to generate quantitative data, multiple reactions are required for each analysis. While this type of assay is very sensitive and quantitative, these assays require multiple steps in development, execution, and analysis, making them very time-consuming, cumbersome, and expensive. The need to perform a titration reduces the overall throughput of the assay, and the requirement for an internal competitor for each target reduces the multiplexing capacity. These limitations restrict the usefulness of this assay in analysis of large numbers of gene sets.

In order to increase the throughput of the RT-PCR assay, Su et al. (BioTechniques (1997) 22:1107–1113) combined microplate-based RNA extraction with multiplexed RT-PCR. With this method, they demonstrated simultaneous analysis of three different target mRNAs amplified from samples prepared from a 96 well microplate. However, changes in gene expression were only presented qualitatively.

Other methods for targeted mRNA analysis include differential display reverse transcriptase PCR (DDRT-PCR) and RNA arbitrarily primed PCR (RAP-PCR) (see U.S. Pat. No. 5,599,672; Liang and Pardee (1992) Science 257:967–971; Welsh et al. (1992) Nucleic Acids Res. 20:4965–4970). Both methods use random priming to generate RT-PCR fingerprint profiles of transcripts in an unfractionated RNA preparation. The signal generated in these types of analyses is a pattern of bands separated on a sequencing gel. Differentially expressed genes appear as changes in the fingerprint profiles between two samples, which can be loaded in separate wells of the same gel. This type of readout allows identification of both up- and down-regulation of genes in the same reaction, appearing as either an increase or decrease in intensity of a band from one sample to another. However, due to the complexity of the fingerprint profile, amplification products are strongly biased towards more abundant transcripts. Simultaneous amplification of hundreds to thousands of different products dramatically compresses the dynamic range of measurement. The combined result of amplification bias, dynamic range compression and other biases that result from the use of a complex mix of primers eliminates the ability to quantitate relative changes in expression between the different genes in a sample. Furthermore, the methodology is designed for identification of changes in the transcriptional profile of a whole cell, but does not provide any information about the identities of the PCR products. To identify a species, a band must be excised from the gel, subcloned, sequenced, and finally matched to a gene in a sequence database. The complexity of the profile prohibits complete resolution of PCR products on the gel, causing a high incidence of false positives arising from multiple species existing in the same region of the gel. These characteristics make general fingerprinting techniques unsuitable for investigation of already identified transcripts, and precludes a high-throughput quantitative analysis.

The TaqMan assay (Livak et al. (1995) PCR Methods Appl. 4:357–362) is a quenched fluorescent dye system for quantitating targeted mRNA levels in a complex mixture. The assay has good sensitivity and dynamic range, and yields quantitative results. But because detection is based on fluorescence of unfractionated products, it can be multiplexed only to the very low levels (i.e., two to four) as allowed by resolution of emission spectra of the chromaphores. Furthermore, due to overlapping emission spectra, multiplexing reduces the accuracy of quantitation. This limitation makes differential analysis problematic and increases the cost. Also, the assay is performed in real time during thermal cycling, greatly reducing the throughput of the assay.

Nucleic acid microarrays have been developed recently, which have the benefit of assaying for sample hybridization to a large number of probes in a highly parallel fashion. They can be used for quantitation of mRNA expression levels, and dramatically surpass the above mentioned techniques in terms of multiplexing capability. These arrays comprise short DNA sequences, PCR products, or mRNA isolates fixed onto a solid surface, which can then be used in a hybridization reaction with a target sample, generally a whole cell extract (see, for example, U.S. Pat. Nos. 5,143,854 and 5,807,522; Fodor et al. (1991) Science 251:767–773; and Schena et al. (1995) Science 270:467–470). Microarrays can be used to measure the expression levels of several thousands of genes simultaneously, generating a gene expression profile of the entire genome of relatively simple organisms. Each reaction, however, is performed with a single sample against a very large number of gene probes. As a consequence, microarray technology does not facilitate high throughput analysis of very large numbers of unique samples against an array of known probes.

The present invention addresses the need for gene expression detection and quantitation methodologies by providing novel methods for analyzing gene expression, systems for implementing these techniques, compositions for preparing a plurality of amplification products from a plurality of mRNA target sequences, and related pools of amplification products. The methods of the present invention include the steps of (a) obtaining a plurality of target cDNA sequences; (b) multiplex amplifying the target sequences using a plurality of target-specific primers and one or more universal primers; (c) separating one or more members of the resulting plurality of amplification products; (d) detecting the one or more members of the plurality of amplification products, thereby generating a set of gene expression data; (e) storing the data in a database; and (f) performing a comparative analysis on the set of gene expression data, thereby analyzing the gene expression. The methods of the invention are highly sensitive; have a wide dynamic range; are rapid and inexpensive; have a high throughput; and allow the simultaneous differential analysis of a defined set of genes. The methods, compositions and kits of the invention also provide tools for gene expression data collection and relational data analysis.

Methods for Quantitating Gene Expression Levels

The controlled expression of particular genes or groups of genes in a cell is the molecular basis for regulation of biological processes and, ultimately, for the physiological or pathological state of the cell. Knowledge of the "expression profile" of a cell is of key importance for answering many biological questions, including the nature and mechanism of cellular changes, or the degree of differentiation of a cell, organ, or organism. Furthermore, the factors involved in determining the expression profile may lead to the discovery of cures that could reverse an adverse pathological or physiological condition. A defined set of genes can be demonstrated to serve as indicators of a particular state of a cell, and can therefore serve as a model for monitoring the cellular profile of gene expression in that state.

The pharmaceutical drug discovery process has traditionally been dominated by biochemical and enzymatic studies of a designated pathway. Although this approach has been productive, it is very laborious and time-consuming, and is generally targeted to a single gene or defined pathway. Molecular biology and the development of gene cloning have dramatically expanded the number of genes that are potential drug targets, and this process is accelerating rapidly as a result of the progress made in sequencing the human genome. In addition to the growing set of available genes, techniques such as the synthesis of combinatorial chemical libraries have created daunting numbers of candidate drugs for screening. In order to capitalize on these available materials, methods are needed that are capable of extremely fast and inexpensive analysis of gene expression levels.

The present invention provides novel methods for the analysis of changes in expression levels of a set of genes. These methods include providing a plurality of target sequences, which are then analyzed simultaneously in a multiplexed reaction. Multiplexing the analysis improves the accuracy of quantitation; for example, signals from one or more target genes can be compared to an internal control. Multiplexing also reduces the time and cost required for analysis. Thus, the methods of the present invention provide for rapid generation of a differential expression profile of a defined set of genes, through the comparison of data from multiple reactions.

The methods of the present invention include the steps of (a) obtaining a plurality of target nucleic acid sequences, generally cDNA sequences; (b) multiplex amplifying the target sequences using a plurality of target-specific primers and one or more universal primers; (c) separating one or more members of the resulting plurality of amplification products; (d) detecting the one or more members of the plurality of amplification products, thereby generating a set of gene expression data; (e) storing the data in a database; and (f) performing a comparative analysis on one or more components of the set of gene expression data, thereby analyzing the gene expression. In an alternative embodiment, the methods of the present invention include the steps of obtaining cDNA from a plurality of samples for a plurality of target sequences; performing a plurality of multiplexed amplifications of the target sequences, thereby producing a plurality of multiplexed amplification products; pooling the plurality of multiplexed amplification products; separating the plurality of multiplexed amplification products; detecting the plurality of multiplexed amplification products, thereby generating a set of gene expression data; storing the set of gene expression data in a database; and performing a comparative analysis of the set of gene expression data. In yet another embodiment, the methods of the present invention include the steps of (a) obtaining cDNA from multiple samples; (b) amplifying a plurality of target sequences from the cDNA, thereby producing a multiplex of amplification products; (c) separating and detecting the amplification products using a high throughput platform, wherein detecting generates a set of gene expression data; (d) storing the set of gene expression data in a database; and (e) performing a comparative analysis of the set of gene expression data. In a further embodiment, the present invention provides methods for analyzing gene expression, including the steps of (a) obtaining cells, e.g. culturing one of several designated cell lines; (b) optionally subjecting a set of the cultures to a specified treatment; (c) lysing the cells and isolating one or more RNA molecules; (d) synthesizing cDNA first strand molecules from a designated set of the mRNA molecules; (e) quantitatively amplifying the resulting set of cDNA products using target-specific primers in early rounds, coupled with amplifying the whole set by universal primers that have partial homology with all of the target-specific primers, and that contain a detectable label, preferably a fluorescent chromaphore, on at least one of the primers; (f) optionally pooling products of two or more separate reactions; (g) physically separating amplified products according to their length; (h) detecting and quantitating the separated amplification products, for example, by deconvolution of data from any species of the same length (arising from reactions that were pooled); (i) determining the relative abundance levels using an internal reference target; (j) storing the information in a gene expression database; and (k) performing a comparative analysis of the expression patterns. Each aspect of these methods of the present invention is addressed in greater detail below.

Sources of Target Sequences

Target sequences for use in the methods of the present invention are obtained from a number of sources. For example, the target sequences can be derived from organisms or from cultured cell lines. Cell types utilized in the present invention can be either prokaryotic or eukaryotic cell types and/or organisms, including, but not limited to, animal cells, plants, yeast, fungi, bacteria, viruses, and the like. Target sequences can also be obtained from other sources, for example, needle aspirants or tissue samples from an organism (including, but not limited to, mammals such as mice, rodents, guinea pigs, rabbits, dogs, cats, primates and humans; or non-mammalian animals such as nematodes, frogs, amphibians, various fishes such as the zebra fish, and other species of scientific interest), non-viable organic samples or their derivatives (such as a cell extract or a purified biological sample), or environmental sources, such as an air or water sample. Furthermore, target sequences can also be commercially or synthetically prepared, such as a chemical, phage, or plasmid library. DNA and/or RNA sequences are available from a number of commercial sources, including The Midland Certified Reagent Company (mcrcatoligos.com), The Great American Gene Company (www.genco.com), ExpressGen Inc. (www.expressgen.com), Operon Technologies Inc. (Alameda, Calif.) and many others.

Cell lines which can be used in the methods of the present invention include, but are not limited to, those available from cell repositories such as the American Type Culture Collection (www.atcc.org), the World Data Center on Microorganisms (wdcm.nig.ac.jp), European Collection of Animal Cell Culture (www.ecacc.org) and the Japanese Cancer Research Resources Bank (cellbank.nihs.go.jp). These cell lines include, but are not limited to, the following cell lines: 293, 293Tet-Off, CHO-AA8 Tet-Off, MCF7, MCF7 Tet-Off, LNCap, T-5, BSC-1, BHK-21, Phinx-A, 3T3, HeLa, PC3, DU145, ZR 75-1, HS 578-T, DBT, Bos, CV1, L-2, RK13, HTTA, HepG2, BHK-Jurkat, Daudi, RAMOS, KG-1, K562, U937, HSB-2, HL-60, MDAHB231, C2C12, HTB-26, HTB-129, HPIC5, A-431, CRL-1573, 3T3L1, Cama-1, J774A.1, HeLa 229, PT-67, Cos7, OST7, HeLa-S, THP-1, and NXA. Additional cell lines for use in the methods and matrices of the present invention can be obtained, for example, from cell line providers such as Clonetics Corporation (Walkersville, Md.; www.clonetics.com). Optionally, the plurality of target sequences are derived from cultured cells optimized for the analysis of a particular disease area of interest, e.g., cancer, inflammation, cardiovascular disease, diabetes, infectious diseases, proliferative diseases, an immune system disorder, or a central nervous system disorder.

A variety of cell culture media are described in *The Handbook of Microbiological Media,* Atlas and Parks (eds) (1993, CRC Press, Boca Raton, Fla.). References describing the techniques involved in bacterial and animal cell culture include Sambrook et al., *Molecular Cloning—A Laboratory Manual* (2nd Ed.), Vol. 1–3 (1989, Cold Spring Harbor Laboratory, Cold Spring Harbor, N.Y.); *Current Protocols in Molecular Biology,* F. M. Ausubel et al., eds., Current Protocols, (a joint venture between Greene Publishing Associates, Inc. and John Wiley & Sons, Inc., supplemented through 2000); Freshney, *Culture of Animal Cells, a Manual of Basic Technique,* third edition (1994, Wiley-Liss, New York) and the references cited therein; Humason, *Animal Tissue Techniques,* fourth edition (1979, W. H. Freeman and Company, New York); and Ricciardelli, et al. (1989) *In Vitro Cell Dev. Biol.* 25:1016–1024. Information regarding plant cell culture can be found in *Plant Cell and Tissue Culture in Liquid Systems,* by Payne et al. (1992, John Wiley & Sons, Inc. New York, N.Y.);*Plant Cell, Tissue and Organ Culture: Fundamental Methods* by Gamborg and Phillips, eds. (1995, Springer Lab Manual, Springer-Verlag, Berlin), and is also available in commercial literature such as the *Life Science Research Cell Culture Catalogue* (1998) from Sigma-Aldrich, Inc (St Louis, Mo.) (Sigma-LSRCCC) and the *Plant Culture Catalogue* and supplement (1997) also from Sigma-Aldrich, Inc (St Louis, Mo.) (Sigma-PCCS).

In an exemplary embodiment of methods of the present invention, either primary or immortalized (or other) cell lines are grown in a master flask, then trypsinized (if they are adherent) and transferred to a 96-well plate, seeding each well at a density of $10^4$ to $10^6$ cells/well. If the gene expression profile in response to a chemical treatment is sought, the chemical agent of choice is prepared in a range of concentrations. After a time of recovery and growth as appropriate to the cell line, cells are exposed to the chemical for a period of time that will not adversely impact the viability of the cells. Preferably, assays include a range of chemical concentrations and exposure times, and would include replicate samples. After treatment, medium is removed and cells are immediately lysed.

In further embodiments of cell culture, formats other than a 96-well plate may be used. Other multiwell or microplate formats containing various numbers of wells, such as 6, 12, 48, 384, 1536 wells, or greater, are also contemplated. Culture formats that do not use conventional flasks, as well as microtiter formats, may also be used.

Treatment of Cells

The cells lines or sources containing the target nucleic acid sequences, are optionally subjected to one or more specific treatments, or in the case of organisms, may already be in different pathological or physiological stages that induce changes in gene expression. For example, a cell or cell line can be treated with or exposed to one or more chemical or biochemical constituents, e.g., pharmaceuticals, pollutants, DNA damaging agents, oxidative stress-inducing agents, pH-altering agents, membrane-disrupting agents, metabolic blocking agent; a chemical inhibitors, cell surface receptor ligands, antibodies, transcription promoters/enhancers/inhibitors, translation promoters/enhancers/inhibitors, protein-stabilizing or destabilizing agents, various toxins, carcinogens or teratogens, characterized or uncharacterized chemical libraries, proteins, lipids, or nucleic acids. Optionally, the treatment comprises an environmental stress, such as a change in one or more environmental parameters including, but not limited to, temperature (e.g. heat shock or cold shock), humidity, oxygen concentration (e.g., hypoxia), radiation exposure, culture medium composition, or growth saturation. Alternatively, cultured cells may be exposed to other viable organisms, such as pathogens or other cells, to study changes in gene-expression that result from biological events, such as infections or cell-cell interactions. Responses to these treatments may be followed temporally, and the treatment can be imposed for various times and at various concentrations. Target sequences can also be derived from cells or organisms exposed to multiple specific treatments as described above, either concurrently or in tandem (i.e., a cancerous tissue sample may be further exposed to a DNA damaging agent while grown in an altered medium composition).

RNA Isolation

In some embodiments of the present invention, total RNA is isolated from samples for use as target sequences. Cellular samples are lysed once culture with or without the treatment is complete by, for example, removing growth medium and adding a guanidinium-based lysis buffer containing several components to stabilize the RNA. In some embodiments of the present invention, the lysis buffer also contains purified RNAs as controls to monitor recovery and stability of RNA from cell cultures. Examples of such purified RNA templates include the Kanamycin Positive Control RNA from Promega (Madison, Wis.), and 7.5 kb Poly(A)-Tailed RNA from Life Technologies (Rockville, Md.). Lysates may be used immediately or stored frozen at, e.g., −80° C.

Optionally, total RNA is purified from cell lysates (or other types of samples) using silica-based isolation in an automation-compatible, 96-well format, such as the Rneasy® purification platform (Qiagen, Inc.; Valencia, Calif.). Alternatively, RNA is isolated using solid-phase oligo-dT capture using oligo-dT bound to microbeads or cellulose columns. This method has the added advantage of isolating mRNA from genomic DNA and total RNA, and allowing transfer of the mRNA-capture medium directly into the reverse transcriptase reaction. Other RNA isolation methods are contemplated, such as extraction with silica-coated beads or guanidinium. Further methods for RNA isolation and preparation can be devised by one skilled in the art.

Alternatively, the methods of the present invention are performed using crude cell lysates, eliminating the need to isolate RNA. RNAse inhibitors are optionally added to the crude samples. When using crude cellular lysates, genomic DNA could contribute one or more copies of target sequence, depending on the sample. In situations in which the target sequence is derived from one or more highly expressed genes, the signal arising from genomic DNA may not be significant. But for genes expressed at very low levels, the background can be eliminated by treating the samples with DNAse, or by using primers that target splice junctions. For example, one of the two target-specific primers could be designed to span a splice junction, thus excluding DNA as a template. As another example, the two target-specific primers are designed to flank a splice junction, generating larger PCR products for DNA or unspliced mRNA templates as compared to processed mRNA templates. One skilled in the art could design a variety of specialized priming applications that would facilitate use of crude extracts as samples for the purposes of this invention.

Primer Design and Multiplex Strategies

Multiplex amplification of the target sequence involves combining the plurality of target sequences with a plurality of target-specific primers and one or more universal primers, to produce a plurality of amplification products. A multiplex set of target sequences optionally comprises between about two targets and about 100 targets. In one embodiment of the present invention, the multiplex reaction includes at least 5 target sequences, but preferably at least ten targets or at least fifteen targets. Multiplexes of much larger numbers (e.g., about 20, about 50, about 75 and greater) are also contemplated.

In one embodiment of the methods of the present invention, at least one of the amplification targets in the multiplex set is a transcript that is endogenous to the sample and has been independently shown to exhibit a fairly constant expression level (for example, a "housekeeping" gene). The signal from this endogenous reference sequence provides a control for converting signals of other gene targets into relative expression levels. Optionally, a plurality of control mRNA targets/reference sequences that have relatively constant expression levels may be included in the multiplexed amplification to serve as controls for each other. Alternatively, a defined quantity of an exogenous purified RNA species is added to the multiplex reaction or to the cells, for example, with the lysis reagents. Almost any purified, intact RNA species can be used, e.g. the Kanamycin Positive Control RNA or the 7.5 kb Poly(A)-Tailed RNA mentioned previously. This exogenously-added amplification target provides a way to monitor the recovery and stability of RNA from cell cultures. It can also serve as an exogenous reference signal for converting the signals obtained from the sample mRNAs into relative expression levels. In still another embodiment, a defined quantity of a purified DNA species is added to the PCR to provide an exogenous reference target for converting the signals obtained from sample mRNA targets into relative expression levels.

In one embodiment of the present invention, once the targets that comprise a multiplex set are determined, primer pairs complementary to each target sequence are designed, including both target-specific and universal primers. This can be accomplished using any of several software products that design primer sequences, such as OLIGO (Molecular Biology Insights, Inc., CO), Gene Runner (Hastings Software Inc., NY), or Primer3 (The Whitehead Institute, MA). FIG. 1 illustrates the elements of design of exemplary target-specific primers (TSPs) and universal primers (UPs). Target specific primers (TSP1, TSP2, TSP3, TSP4 and TSP5) are comprised of at least two portions. One portion, shown as a solid line within the 5' region of each of the five TSP sequences, includes a region complementary to a selected "universal sequence." The universal sequence is utilized to allow amplification of multiple targets (having divergent sequences) while using the same primer (e.g., the UP). The universal sequence is contained only in the primers, and preferably is not present in any nucleic acid (or complement thereof) provided by the sample being tested. A second portion of the TSPs, shown as variable lines (solid, dotted, dashed, etc) within the 3' region of the sequence, represents the sequence that is complementary to and will hybridize with one of a plurality of designated target sequences In FIG. 1, a single universal primer (labeled as "UP") is depicted; however, multiple universal primers having different or unique sequences or labels can be employed in the methods of the present invention. Optionally, the primer design also includes consideration of properties beyond the encoded sequence of the primer, such as annealing temperature, 3'-end hybridization stability, and minimization of sequences that would allow annealing among the primers themselves.

Oligonucleotide primers are typically prepared by the phosphoramidite approach. In this automated, solid-phase procedure, each nucleotide is individually added to the 5'-end of the growing oligonucleotide chain, which is in turn attached at the 3'-end to a solid support. The added nucleotides are in the form of trivalent 3'-phosphoramidites that are protected from polymerization by a dimethoxytrityl ("DMT") group at the 5'-position. After base induced phosphoramidite coupling, mild oxidation to give a pentavalent phosphotriester intermediate and DMT removal provides a new site for oligonucleotide elongation. These syntheses may be performed on, for example, a Perkin Elmer/Applied Biosystems Division DNA synthesizer. The oligonucleotide primers are then cleaved off the solid support, and the phosphodiester and exocyclic amino groups are deprotected with ammonium hydroxide.

Nucleic Acid Hybridization

The length of complementary sequence between each primer and its binding partner (i.e. the target sequence or the universal sequence) should be sufficient to allow hybridization of the primer only to its target within a complex sample at the annealing temperature used for the PCR. A complementary sequence of, for example, about 15, 16, 17, 18, 19, 20, 21, 22, 23, 24, or 25 or more nucleotides is preferred for both the target-specific and universal regions of the primers. A particularly preferred length of each complementary region is about 20 bases, which will promote formation of stable and specific hybrids between the primer and target.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes,* part I, chapter 2, "Overview of principles of hybridization and the strategy of nucleic acid probe assays," (Elsevier, N.Y.), as well as in Ausubel, supra. Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

"Stringent hybridization wash conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched primer. Very stringent conditions are selected to be equal to the $T_m$ for a particular primer.

The $T_m$ is the temperature of the nucleic acid duplexes indicates the temperature at which the duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increase sensitivity, but can product nonspecific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds., *Molecular Biomethods Handbook* (Humana Press, Inc. 1998) (hereinafter "Rapley and Walker"), which is incorporated herein by reference in its entirety for all purposes.

Thus, one measure of stringent hybridization is the ability of the primer to hybridize to one or more of the target nucleic acids (or complementary polynucleotide sequences thereof) under highly stringent conditions. Stringent hybridization and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a target nucleic acid, and complementary polynucleotide sequences thereof, binds to a perfectly matched complementary nucleic acid.

A target nucleic acid is said to specifically hybridize to a primer nucleic acid when it hybridizes at least ½ as well to the primer as to a perfectly matched complementary target, i.e., with a signal to noise ratio at least ½ as high as hybridization of the primer to the target under conditions in which the perfectly matched primer binds to the perfectly matched complementary target with a signal to noise ratio that is at least about 2.5×–10×, typically 5×–10× as high as that observed for hybridization to any of the unmatched target nucleic acids.

Optionally, primers are designed such that the annealing temperature of the universal sequence is higher/greater than that of the target-specific sequences. Method employing these primers further include increasing the annealing temperature of the reaction after the first few rounds of amplification. This increase in reaction temperature suppresses further amplification of sample nucleic acids by the TSPs, and drives amplification by the UP. Depending on the application envisioned, one skilled in the art can employ varying conditions of hybridization to achieve varying degrees of selectivity of primer towards the target sequence. For example, varying the stringency of hybridization or the position of primer hybridization can reveal divergence within gene families.

Optionally, each candidate primer is shown or proven to be compatible with the other primers used in a multiplex reaction. In a preferred embodiment, each target-specific primer pair produces a single amplification product of a predicted size from a sample minimally containing all of the targets of the multiplex, and more preferably from a crude RNA mixture. Preferably, amplification of each individual target by its corresponding primers is not inhibited by inclusion of any other primers in the multiplex. None of the primers, either individually or in combination, should produce spurious products. These issues are easily addressed by one of skill in the art without the need for excessive undue experimentation.

Inherent Properties and Labels

Primer sequences are optionally designed to accommodate one or more detection techniques that can be employed while performing the methods of the present invention. For example, detection of the amplification products is optionally based upon one or more inherent properties of the amplification products themselves, such as mass or mobility. Other embodiments utilize methods of detection based on monitoring a label associated with the PCR products. In these embodiments, generally one or more of the universal primers contains the label. Optionally, the label is a fluorescent chromaphore. A fluorescent label may be covalently attached, noncovalently intercalated, or may be an energy transfer label. Other useful labels include mass labels, which are incorporated into amplification products and released after the reaction for detection, chemiluminescent labels, electrochemical and infrared labels, isotopic derivatives, nanocrystals, or any of various enzyme-linked or substrate-linked labels detected by the appropriate enzymatic reaction.

One preferred embodiment of the methods of the present invention includes the use and detection of one or more fluorescent labels. Generally, fluorescent molecules each display a distinct emission spectrum, thereby allowing one to employ a plurality of fluorescent labels in a multiplexed reaction, and then separate the mixed data into its component signals by spectral deconvolution. Exemplary fluorescent labels for use in the methods of the present invention include a single dye covalently attached to the molecule being detected, a single dye noncovalently intercalated into product DNA, or an energy-transfer fluorescent label.

Other embodiments of labeling include mass labels, which are incorporated into amplification products and released after the reaction for detection; chemiluminescent, electrochemical, and infrared labels; radioactive isotopes; and any of various enzyme-linked or substrate-linked labels detectable by the appropriate enzymatic reaction. Many other useful labels are known in the art, and one skilled in the art can envision additional strategies for labeling amplification products of the present invention.

Cleavable Linkages and Size-Shifting of Amplification Products

Primers can also be designed to produce amplification products having sizes which can selectively be changed, or "shifted" after amplification, in order to better resolve the amplification products prior to or during detection. For example, a primer can be designed to incorporate a restriction enzyme site within a portion of the amplified product. The products of this reaction can then optionally be cleaved enzymatically to generate size-shifted amplification products. Alternatively, primers can be designed to incorporate various chemically-cleavable linkages, mass labels, or other linkers which can optionally be used in the detection of one or more of the amplification products.

Linking groups, or linkers, can also be incorporated into the primers of the present invention. Linking groups of use in the present invention can have a range of structures, substituents and substitution patterns. They can, for example be derivitized with nitrogen, oxygen and/or sulfur containing groups which are pendent from, or integral to, the linker group backbone. Examples include, polyethers, polyacids (polyacrylic acid, polylactic acid), polyols (e.g., glycerol,), polyamines (e.g., spermine, spermidine) and molecules having more than one nitrogen, oxygen and/or sulfur moiety (e.g., 1,3-diamino-2-propanol, taurine). See, for example, Sandler et al. Organic Functional Group Preparations 2nd Ed., Academic Press, Inc. San Diego 1983.

Methods for preparing linkers that can be incorporated into primers for use in the methods of the present invention are known in the art. Numerous linking groups compatible with phosphoramidite chemistry are commercially available (Glen Research, Sterling, Va.) and can readily be incorporate into oligonucleotides during automated synthesis procedures.

One of skill will recognize that a linker that is appropriate for incorporation into a nucleic acid oligomer synthesis can also be utilized to derivatize a nucleic acid monomer. For example, chemically cleavable primers can be used in the amplification step of the methods of the present invention. In these embodiments, one or more of the primers used in amplification contain a chemical linkage, such as a thiophosphate moiety, that can be selectively cleaved, generating two separate fragments from the primer. Cleavage is optionally performed after the amplification reaction, e.g., by removing a fixed number of nucleotides from the 5' end of products made from that primer. Design and use of such primers is described in detail in, for example, Li et al (Electrophoresis (1999) 20:1258–1265), PCT publication WO 96/37630 (Monforte et al.) and U.S. Pat. No. 5,700,642 (Monforte et al.) and U.S. Pat. No. 6,090,558 (Butler et al.), which are incorporated herein by reference in their entirety for all purposes.

Exemplary Primer Designs for Use in a Multiplexed Amplification Reaction

A preferred embodiment of the invention utilizes a combination of TSPs that will hybridize with one of a plurality of designated target sequences, and universal primers (UPs) for amplification of multiple targets in the multiplexed reaction. Optionally, the primary way of separating the signals of the multiplexed amplification is according to product sizes. Alternatively, the signals can be resolved using differential labeling to separate signals from products of similar size. To separate products according to size, the predicted sizes must be considered in primer design. FIG. 1 illustrates the elements of design of these primers. Each of the TSPs has a universal sequence within the 5' region, which is shared among the primers, but not contained in the original template (i.e. the target sequence). This universal sequence may be the same or different for the forward and reverse TSPs. Following the 3' end of the universal sequence is a target-specific sequence for annealing to and amplifying the target sequence (e.g., gene) of interest.

The universal primer is composed of the universal sequence held in common within the 5' regions of the TSPs. If a single UP is to be used, the universal sequence will be the same within all TSPs. If a UP pair is to be used, the universal sequence will be different in the forward and reverse primers of the TSPs. The UP may also contain a detectable label on at least one of the primers, such as a fluorescent chromaphore. Both the target-specific and universal sequences are of sufficient length and sequence complexity to form stable and specific duplexes, allowing amplification and detection of the target gene.

Elimination of Variations in Primer Annealing Efficiency

Variations in primer length and sequence can also have a large impact on the efficiency with which primers anneal to their target and prime replication. In a typical multiplexed reaction in which each product is amplified by a unique primer pair, the relative quantities of amplified products may be significantly altered from the relative quantities of targets due to difference in annealing efficiencies. Embodiments of the methods of the present invention that couple the use of target-specific primers and universal primers eliminates this bias, producing amplification products that accurately reflect relative mRNA levels.

Coupled Target-specific and Universal Priming of the PCR

In the methods of the present invention, the amounts of each designated target are amplified to improve the sensitivity and dynamic range of the assay. In some embodiments to monitor gene expression, cellular RNA is isolated and reverse transcribed to obtain cDNA, which is then used as template for amplification. In other embodiments, cDNA may be provided and used directly. The primers described for use in the present invention can be used in any one of a number of template-dependent processes that amplify sequences of the target gene and/or its expressed transcripts present in a given sample. Other types of templates may also be used, such as tRNA, rRNA, or other transcription products, genomic DNA, viral nucleic acids, and synthetic nucleic acid polymers. Several methods described below are contemplated.

A preferred embodiment of the methods of the present invention employs PCR, which is described in detail in U.S. Pat. No. 4,683,195 (Mullis et al.), U.S. Pat. No. 4,683,202 (Mullis), and U.S. Pat. No. 4,800,159 (Mullis et al.), and in *PCR Protocols A Guide to Methods and Applications* (Innis et al., eds.) Academic Press Inc. San Diego, Calif. (1990). PCR utilizes pairs of primers having sequences complimentary to opposite strands of target nucleic acids, and positioned such that the primers are converging. The primers are incubated with template DNA under conditions that permit selective hybridization. Primers may be provided in double-stranded or single-stranded form, although the single-stranded form is preferred. If the target gene(s) sequence is present in a sample, the primers will hybridize to form a nucleic-acid:primer complex. An excess of deoxynucleoside triphosphates is added, along with a thermostable DNA polymerase, e.g. Taq polymerase. If the target gene(s) :primer complex has been formed, the polymerase will extend the primer along the target gene(s) sequence by adding nucleotides. After polymerization, the newly-synthesized strand of DNA is dissociated from its complimentary template strand by raising the temperature of the reaction mixture. When the temperature is subsequently lowered, new primers will bind to each of these two strands of DNA, and the process is repeated. Multiple cycles of raising and lowering the temperature are conducted, with a round of replication in each cycle, until a sufficient amount of amplification product is produced.

FIG. 2 illustrates the TSP-UP coupled priming strategy. Heavier lines represent a DNA template; thinner lines depict the oligonucleotide primers. Primer nomenclature is as described in the legend to FIG. 1. The lower case "f" and "r" in the primer names indicate a forward or reverse orientation. Lines "A," "B," "C," and "D" represent unique nucleic acid sequences, and "A'," "B'," "C'," and "D'" indicate their respective complementary sequences. "B" and "C" sequences derive from the template; "A" and "D" sequences derive from universal primer sequences. Arrowheads indicate directionality. A vertical bar indicates an endpoint of the DNA strand. The first set of reactions (first arrow) occur in the early PCR cycles (for example, in only the first and second PCR cycles); in these reaction, primarily the TSPs are used as primers, and the resulting products will have UP sequences added to both ends, flanking the amplified target sequence. The second set of reactions (second, reiterative arrow) occur in all subsequent PCR cycles; both TSP and UP primers are used, but the UPs dominate when present in molar excess over the TSPs.

In early rounds of the amplification, replication is primed primarily by the TSPs. The first round will add the universal sequence to the 5' regions of the amplification products. The second cycle will generate sequence complementary to the universal sequence within the 3' region of the complementary strand, creating a template that can be amplified by the universal primers alone. Optionally, the reaction is designed to contain limiting amounts of each of the TSPs and a molar excess of the UP, such that the UP will generally prime replication once its complementary sequence has been established in the template. The molar excess of UP over a TSP can range from about 5:1 to about 100:1; optionally, the reaction utilizes approximately 10:1 molar excess of UP over the amount of each TSP. Because all of the TSPs contain the same universal sequence, the same universal primer will amplify all targets in the multiplex, eliminating the quantitative variation that results from amplification from different primers.

Amplification Methods

In a preferred embodiment of the methods of the present invention, RNA is converted to cDNA using a target-specific primer complementary to the RNA for each gene target being monitored in the multiplex set in a reverse-transcription (RT) reaction. Methods of reverse transcribing RNA into cDNA are well known, and described in Sambrook, supra. Alternative methods for reverse transcription utilize thermostable DNA polymerases, as described in the art. As an exemplary embodiment, avian myeloblastosis virus reverse transcriptase (AMV-RT), or Maloney murine leukemia virus reverse transcriptase (MoMLV-RT) is used, although other enzymes are contemplated. An advantage of using target-specific primers in the RT reaction is that only the desired sequences are converted into a PCR template. No superfluous primers or cDNA products are carried into the subsequent PCR amplification.

In another embodiment of the amplifying step, RNA targets are reverse transcribed using non-specific primers, such as an anchored oligo-dT primer, or random sequence primers. An advantage of this embodiment is that the "unfractionated" quality of the mRNA sample is maintained because the sites of priming are non-specific, i.e., the products of this RT reaction will serve as template for any desired target in the subsequent PCR amplification. This allows samples to be archived in the form of DNA, which is more stable than RNA.

In other embodiments of the methods of the present invention, transcription-based amplification systems (TAS) are used, such as that first described by Kwoh et al. (Proc. Natl. Acad. Sci. (1989) 86(4):1173–7), or isothermal transcription-based systems such as 3SR (Self-Sustained Sequence Replication; Guatelli et al. (1990) Proc. Natl. Acad. Sci. 87:1874–1878) or NASBA (nucleic acid sequence based amplification; Kievits et al. (1991) J Virol Methods. 35(3):273–86). In these methods, the mRNA target of interest is copied into cDNA by a reverse transcriptase. The primer for cDNA synthesis includes the promoter sequence of a designated DNA-dependent RNA polymerase 5' to the primer's region of homology with the template. The resulting cDNA products can then serve as templates for multiple rounds of transcription by the appropriate RNA polymerase. Transcription of the cDNA template rapidly amplifies the signal from the original target mRNA. The isothermal reactions bypass the need for denaturing cDNA strands from their RNA templates by including RNAse H to degrade RNA hybridized to DNA.

In other embodiments, amplification is accomplished by used of the ligase chain reaction (LCR), disclosed in European Patent Application No. 320,308 (Backman and Wang), or by the ligase detection reaction (LDR), disclosed in U.S. Pat. No. 4,883,750 (Whiteley et al.). In LCR, two probe pairs are prepared, which are complimentary each other, and to adjacent sequences on both strands of the target. Each pair will bind to opposite strands of the target such that they abut. Each of the two probe pairs can then be linked to form a single unit, using a thermostable ligase. By temperature cycling, as in PCR, bound ligated units dissociate from the target, then both molecules can serve as "target sequences" for ligation of excess probe pairs, providing for an exponential amplification. The LDR is very similar to LCR. In this variation, oligonucleotides complimentary to only one strand of the target are used, resulting in a linear amplification of ligation products, since only the original target DNA can serve as a hybridization template. It is used following a PCR amplification of the target in order to increase signal.

In further embodiments, several methods generally known in the art would be suitable methods of amplification. Some additional examples include, but are not limited to, strand displacement amplification (Walker et al. (1992) Nucleic Acids Res. 20:1691–1696), repair chain reaction (REF), cyclic probe reaction (REF), solid-phase amplification, including bridge amplification (Mehta and Singh (1999) BioTechniques 26(6): 1082–1086), rolling circle amplification (Kool, U.S. Pat. No. 5,714,320), rapid amplification of cDNA ends (Frohman (1988) Proc. Natl. Acad. Sci. 85:8998–9002), and the "invader assay" (Griffin et al. (1999) Proc. Natl. Acad. Sci. 96: 6301–6306).

Attenuation of Strong Signals

The set of targets included in a multiplex reaction generally all yield signal strengths within the dynamic range of the detection platform used in order for quantitation of gene expression to be accurate. In some embodiments, it may be desirable or necessary to include a very highly expressed gene in a multiplex assay. However, the highly-expressed gene can impact the accuracy of quantitation for other genes expressed at very low levels if its signal is not attenuated. The methods of the current invention provide ways for attenuating the signals of relatively abundant targets during the amplification reaction such that they can be included in a multiplexed set without impacting the accuracy of quantitation of that set.

Toward this end, amplification primers are optionally used that block polymerase extension of the 3' end of the primer. One preferred embodiment is modification of the 3'-hydroxyl of the oligonucleotide primer by addition of a phosphate group. Another preferred embodiment is attachment of the terminal nucleotide via a 3'-3' linkage. One skilled in the art can conceive of other chemical structures or modifications that can be used for this purpose. The modified and the corresponding unmodified primer for the highly abundant target are mixed in a ratio empirically determined to reduce that target's signal, such that it falls within the dynamic range of other targets of the multiplex. Preferably, the reverse target-specific primer is modified, thereby attenuating signal by reduction of the amount of template created in the reverse transcriptase reaction.

Another embodiment for signal attenuation entails use of a target-specific primer that contains the target-specific sequence, but no universal primer sequence. This abbreviated primer (sans universal sequence) and the corresponding primer containing the universal sequence within the 5' region are mixed in a ratio empirically determined to reduce that target's signal, such that it then falls within the dynamic range of other targets of the multiplex system.

Multiplex Amplification Strategies

An important embodiment of the methods of the present invention involves the use of various PCR multiplexing strategies that are made possible by the combined use of target-specific and universal primers. An illustration of the fundamental multiplexed reaction is shown in FIG. 3.

The numbers 1 through 6 on the left represent six different reactions occurring simultaneously in a single mixture. Column A represents the six target sequences of the multiplex. Column B depicts the templates and primers in the PCR amplification. Lines shown as parallel and having opposite directionality represent complementary sequences. The templates are initially single-stranded mRNA molecules, but eventually are predominantly DNA amplification products that serve as template in subsequent cycles. Messenger RNA is converted to cDNA by the action of reverse transcriptase polymerization from the target-specific reverse primers (TSPr1–6) for each of the six targets. The six target-specific forward primers (TSPf1–6) and the universal forward and reverse primers (UPf1–6, UPr1–6) are added along with a thermostable polymerase to generate the second strand of cDNA, followed by PCR amplification. The drawings in Column B show single-stranded templates with the TSPs aligned (depicted as parallel) at their sites of hybridization. The UP can anneal to target DNA only after its complementary universal sequence is added to the opposite strand through replication across the 5' region of the TSP. Column C shows the products of PCR amplification. Products contain the target sequences (TS1–6) that were the targets of amplification, flanked by the universal primer sequences (UP) that were added to the ends of the target sequences by the target-specific primers. The TSPf and TSPr primers are specific, so by definition they will all be unique. However, the two universal primers may be the same sequence as each other or different sequences, i.e., the UPf may be the same sequence as the UPr. Furthermore, subsets of target sequences in the multiplex set may be amplified by different UPs, i.e., the UPf1–6 primers and/or UPr1–6 primers may be of one or multiple sequences.

All of these examples are variations on the fundamental RT-PCR assay shown in FIG. 3. For the sake of simplicity, only strategies using fluorescent dyes are illustrated, although many of the other labeling strategies previously discussed could be applied.

Data Collection

The number of species than can be detected within a mixture depends primarily on the resolution capabilities of the separation platform used, and the detection methodology employed. A preferred embodiment of the separation step of the methods of the present invention is based upon size-based separation technologies. Once separated, individual species are detected and quantitated by either inherent physical characteristics of the molecules themselves, or detection of a label associated with the DNA.

Embodiments employing other separation methods are also described. For example, certain types of labels allow resolution of two species of the same mass through deconvolution of the data. Non-size based differentiation methods (such as deconvolution of data from overlapping signals generated by two different fluorophores) allow pooling of a plurality of multiplexed reactions to further increase throughput.

Optionally, the throughput rate for the detection step is between about 100 and 5000 samples per hour, preferably between about 250 and 2500 samples, and more preferably about 1000 samples per hour per separation system (i.e., one mass spectrometer, one lane of a gel, or one capillary of a capillary electrophoresis device). In order to further reduce assay costs and increase the throughput of the overall process, sample-handling is optionally conducted in a miniaturized format. For the methods of the present invention, miniaturized formats are those conducted at submicroliter volumes, including both microfluidic and nanofluidic platforms. Any or all of the amplification, separation, and/or detection steps of the present can utilize miniaturized formats and platforms. For example, many of the modes of separation described below are presently available in a miniaturized scale.

Separation Methods

Preferred embodiments of the present invention incorporate a step of separating the products of a reaction based on their size differences. The PCR products generated during the multiplex amplification optionally range from about 50 to about 500 bases in length, which can be resolve from one another by size. Any one of several devices may be used for size separation, including mass spectrometry, any of several electrophoretic devices, including capillary, polyacrylamide gel, or agarose gel electrophoresis, or any of several chromatographic devices, including column chromatography, HPLC, or FPLC.

One preferred embodiment for sample analysis is mass spectrometry. Several modes of separation that determine mass are possible, including Time-of-Flight (TOF), Fourier Transform Mass Spectrometry (FTMS), and quadruple mass spectrometry. Possible methods of ionization include Matrix-Assisted Laser Desorption and Ionization (MALDI) or Electrospray Ionization (ESI). A preferred embodiment for the uses described in this invention is MALDI-TOF (Wu, et al. (1993) Rapid Communications in Mass Spectrometry 7: 142–146). This method may be used to provide unfragmented mass spectra of mixed-base oligonucleotides containing between about 1 and about 1000 bases. In preparing the sample for analysis, the analyte is mixed into a matrix of molecules that resonantly absorb light at a specified wavelength. Pulsed laser light is then used to desorb oligonucleotide molecules out of the absorbing solid matrix, creating free, charged oligomers and minimizing fragmentation. The preferred solid matrix material for this purpose is 3-hydroxypicolinic acid (Wu, supra), although others are contemplated.

In another preferred embodiment, the device of the invention is a microcapillary for analysis of nucleic acids obtained from the sample. Microcapillary electrophoresis generally involves the use of a thin capillary or channel, which may optionally be filled with a particular medium to improve separation, and employs an electric field to separate components of the mixture as the sample travels through the capillary. Samples composed of linear polymers of a fixed charge-to-mass ratio, such as DNA, will separate based on size. The high surface to volume ratio of these capillaries allows application of very high electric fields across the capillary without substantial thermal variation, consequently allowing very rapid separations. When combined with confocal imaging methods, these methods provide sensitivity in the range of attomoles, comparable to the sensitivity of radioactive sequencing methods. The use of microcapillary electrophoresis in size separation of nucleic acids has been reported in Woolley and Mathies (Proc. Natl. Acad. Sci. USA (1994) 91:11348–11352).

Capillaries are optionally fabricated from fused silica, or etched, machined, or molded into planar substrates. In many microcapillary electrophoresis methods, the capillaries are filled with an appropriate separation/sieving matrix. Several sieving matrices are known in the art that may be used for this application, including, e.g., hydroxyethyl cellulose, polyacrylamide, agarose, and the like. Generally, the specific gel matrix, running buffers and running conditions are selected to obtain the separation required for a particular application. Factors that are considered include, e.g., sizes of the nucleic acid fragments, level of resolution, or the presence of undenatured nucleic acid molecules. For example, running buffers may include agents such as urea to denature double-stranded nucleic acids in a sample.

Microfluidic systems for separating molecules such as DNA and RNA are commercially available and are optionally employed in the methods of the present invention. For example, the "Personal Laboratory System" and the "High Throughput System" have been developed by Caliper Technologies, Corp. (Mountain View, Calif.). The Agilent 2100, which uses Caliper Technologies' LabChip™ microfluidic systems, is available from Agilent Technologies (Palo Alto, Calif.). Currently, specialized microfluidic devices which provide for rapid separation and analysis of both DNA and RNA are available from Caliper Technologies for the Agilent 2100. See, e.g., the world wide web at calipertech.com.

Other embodiments are generally known in the art for separating PCR amplification products by electrophoresis through gel matrices. Examples include polyacrylamide, agarose-acrylamide, or agarose gel electrophoresis, using standard methods (Sambrook, supra).

Alternatively, chromatographic techniques may be employed for resolving amplification products. Many types of physical or chemical characteristics may be used to effect chromatographic separation in the present invention, including adsorption, partitioning (such as reverse phase), ion-exchange, and size exclusion. Many specialized techniques have been developed for their application including methods utilizing liquid chromatography or HPLC (Katz and Dong (1990) BioTechniques 8(5):546–55; Gaus et al. (1993) J. Immunol. Methods 158:229–236).

In yet another embodiment of the separation step of the present invention, cDNA products are captured by their affinity for certain substrates, or other incorporated binding properties. For example, labeled cDNA products such as biotin or antigen can be captured with beads bearing avidin or antibody, respectively. Affinity capture is utilized on a solid support to enable physical separation. Many types of solid supports are known in the art that would be applicable to the present invention. Examples include beads (e.g. solid, porous, magnetic), surfaces (e.g. plates, dishes, wells, flasks, dipsticks, membranes), or chromatographic materials (e.g. fibers, gels, screens).

Certain separation embodiments entail the use of microfluidic techniques. Technologies include separation on a microcapillary platform, such as designed by ACLARA BioSciences Inc. (Mountain View, Calif.), or the LabChip™ microfluidic devices made by Caliper Technologies Inc. Another recent technology developed by Nanogen, Inc. (San Diego, Calif.), utilizes microelectronics to move and concentrate biological molecules on a semiconductor microchip. The microfluidics platforms developed at Orchid Biosciences, Inc. (Princeton, N.J.), including the Chemtel™ Chip which provides for parallel processing of hundreds of reactions, can be used in the present invention. These microfluidic platforms require only nanoliter sample volumes, in contrast to the microliter volumes required by other conventional separation technologies.

Fabrication of microfluidic devices, including microcapillary electrophoretic devices, has been discussed in detail, e.g., Regnier et al. (Trends Biotechnol. (1999) 17(3):101–6), Deyl et al. (Forensic Sci. Int. (1998) 92:89–124), Effenhauser et al. (Electrophoresis (1997) 18:2203–2213), and U.S. Pat. No. 5,904,824 (Oh). Typically, the methods make use of photolithographic etching of micron-scale channels on a silica, silicon, or other crystalline substrate or chip. In some embodiments, capillary arrays may be fabricated using polymeric materials with injection-molding techniques. These methods can be readily adapted for use in miniaturized devices of the present invention.

Some of the processes usually involved in genetic analysis have been miniaturized using microfluidic devices. For example, PCT publication WO 94/05414 reports an integrated micro-PCR apparatus for collection and amplification of nucleic acids from a specimen. U.S. Pat. No. 5,304,487 (Wilding et al.) and U.S. Pat. No. 5,296,375 (Kricka et al.) discuss devices for collection and analysis of cell-containing samples. U.S. Pat. No. 5,856,174 (Lipshutz et al.) describes an apparatus that combines the various processing and analytical operations involved in nucleic acid analysis.

Additional technologies are also contemplated. For example, Kasianowicz et al. (Proc. Natl. Acad. Sci. USA (1996) 93:13770–13773) describe the use of ion channel pores in a lipid bilayer membrane for determining the length of polynucleotides. In this system, an electric field is generated by the passage of ions through the pores. Polynucleotide lengths are measured as a transient decrease of ionic current due to blockage of ions passing through the pores by the nucleic acid. The duration of the current decrease was shown to be proportional to polymer length. Such a system can be applied as a size separation platform in the present invention.

The target-specific primers and universal primers of the present invention are useful both as reagents for hybridization in solution, such as priming PCR amplification, as well as for embodiments employing a solid phase, such as microarrays. With microarrays, sample nucleic acids such as mRNA or DNA are fixed on a selected matrix or surface. PCR products may be attached to the solid surface via one of the amplification primers, then denatured to provide single-stranded DNA. This spatially-partitioned, single-stranded nucleic acid is then subject to hybridization with selected probes under conditions that allow a quantitative determination of target abundance. In this embodiment, amplification products from each individual multiplexed reaction are not physically separated, but are differentiated by hybridizing with a set of probes that are differentially labeled. Alternatively, unextended amplification primers may be physically immobilized at discreet positions on the solid support, then hybridized with the products of a multiplexed PCR amplification for quantitation of distinct species within the sample. In this embodiment, amplification products are separated by way of hybridization with probes that are spatially separated on the solid support.

Separation platforms may optionally be coupled to utilize two different separation methodologies, thereby increasing the multiplexing capacity of reactions beyond that which can be obtained by separation in a single dimension. For example, some of the RT-PCR primers of a multiplex reaction may be coupled with a moiety that allows affinity capture, while other primers remain unmodified. Samples are then passed through an affinity chromatography column to separate PCR products arising from these two classes of primers. Flow-through fractions are collected and the bound fraction eluted. Each fraction may then be further separated based on other criteria, such as size, to identify individual components.

The invention also includes rapid analytical method using one or more microfluidic handling systems. For example, a subset of primers in a multiplex reaction would contain a hydrophobic group. Separation is then performed in two dimensions, with hydrophilic partitioning in one direction, followed by size separation in the second direction. The use of a combination of dyes can further increase the multiplex size.

Detection Methods

Following separation of the different products of the multiplex, one or more of the member species is detected and/or quantitated. Some embodiments of the methods of the present invention enable direct detection of products. Other embodiments detect reaction products via a label associated with one or more of the amplification primers. Many types of labels suitable for use in the present invention are known in the art, including chemiluminescent, isotopic, fluorescent, electrochemical, inferred, or mass labels, or enzyme tags. In further embodiments, separation and detection may be a multi-step process in which samples are fractionated according to more than one property of the products, and detected one or more stages during the separation process.

One embodiment of the invention requiring no labeling or modification of the molecules being analyzed is detection of the mass-to-charge ratio of the molecule itself. This detection technique is optionally used when the separation platform is a mass spectrometer. An embodiment for increasing resolution and throughput with mass detection is in mass-modifying the amplification products. Nucleic acids can be mass-modified through either the amplification primer or the chain-elongating nucleoside triphosphates. Alternatively, the product mass can be shifted without modification of the individual nucleic acid components, by instead varying the number of bases in the primers. Several types of moieties have been shown to be compatible with analysis by mass spectrometry, including polyethylene glycol, halogens, alkyl, aryl, or aralkyl moieties, peptides (described in, for example, U.S. Pat. No. 5,691,141). Isotopic variants of specified atoms, such as radioisotopes or stable, higher mass isotopes, are also used to vary the mass of the amplification product. Radioisotopes can be detected based on the energy released when they decay, and numerous applications of their use are generally known in the art. Stable (non-decaying) heavy isotopes can be detected based on the resulting shift in mass, and are useful for distinguishing between two amplification products that would otherwise have similar or equal masses. Other embodiments of detection that make use of inherent properties of the molecule being analyzed include ultraviolet light absorption (UV) or electrochemical detection. Electrochemical detection is based on oxidation or reduction of a chemical compound to which a voltage has been applied. Electrons are either donated (oxidation) or accepted (reduction), which can be monitored as current. For both UV absorption and electrochemical detection, sensitivity for each individual nucleotide varies depending on the component base, but with molecules of sufficient length this bias is insignificant, and detection levels can be taken as a direct reflection of overall nucleic acid content.

Several embodiments of the detecting step of the present invention are designed to identify molecules indirectly by detection of an associated label. A number of labels may be employed that provide a fluorescent signal for detection (see, for example, www.probes.com). If a sufficient quantity of a given species is generated in a reaction, and the mode of detection has sufficient sensitivity, then some fluorescent molecules may be incorporated into one or more of the primers used for amplification, generating a signal strength proportional to the concentration of DNA molecules. Several fluorescent moieties, including Alexa 350, Alexa 430, AMCA, BODIPY 630/650, BODIPY 650/665, BODIPY-FL, BODIPY-R6G, BODIPY-TMR, BODIPY-TRX, carboxyfluorescein, Cascade Blue, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red, are generally known in the art and routinely used for identification of discreet nucleic acid species, such as in sequencing reactions. Many of these dyes have emission spectra distinct from one another, enabling deconvolution of data from incompletely resolved samples into individual signals. This allows pooling of separate reactions that are each labeled with a different dye, increasing the throughput during analysis, as described in more detail below.

The signal strength obtained from fluorescent dyes can be enhanced through use of related compounds called energy transfer (ET) fluorescent dyes. After absorbing light, ET dyes have emission spectra that allow them to serve as "donors" to a secondary "acceptor" dye that will absorb the emitted light and emit a lower energy fluorescent signal. Use of these coupled-dye systems can significantly amplify fluorescent signal. Examples of ET dyes include the ABI PRISM BigDye terminators, recently commercialized by Perkin-Elmer Corporation (Foster City, Calif.) for applications in nucleic acid analysis. These chromaphores incorporate the donor and acceptor dyes into a single molecule and an energy transfer linker couples a donor fluorescein to a dichlororhodamine acceptor dye, and the complex is attached to a DNA replication primer.

Fluorescent signals can also be generated by non-covalent intercalation of fluorescent dyes into nucleic acids after their synthesis and prior to separation. This type of signal will vary in intensity as a function of the length of the species being detected, and thus signal intensities must be normalized based on size. Several applicable dyes are known in the art, including, but not limited to, ethidium bromide and Vistra Green. Some intercalating dyes, such as YOYO or TOTO, bind so strongly that separate DNA molecules can each be bound with a different dye and then pooled, and the dyes will not exchange between DNA species. This enables mixing separately generated reactions in order to increase multiplexing during analysis.

Alternatively, technologies such as the use of nanocrystals as a fluorescent DNA label (Alivisatos, et al. (1996) Nature 382:609–11) can be employed in the methods of the present invention. Another method, described by Mazumder, et al. (Nucleic Acids Res. (1998) 26:1996–2000), describes hybridization of a labeled oligonucleotide probe to its target without physical separation from unhybridized probe. In this method, the probe is labeled with a chemiluminescent molecule that in the unbound form is destroyed by sodium sulfite treatment, but is protected in probes that have hybridized to target sequence.

In another embodiment, products may be detected and quantitated by monitoring a set of mass labels, each of which are specifically associated with one species of amplification reaction. The labels are released by either chemical or enzymatic mechanisms after the amplification reaction. Release is followed by size separation of the mixture of labels to quantitate the amount of each species of the amplification reaction. Separation methods that can be employed include mass spectrometry, capillary electrophoresis, or HPLC. Such strategies, and their applications for detection of nucleic acids, have been described in, for example, U.S. Pat. No. 6,104,028 (Hunter et al.) and U.S. Pat. No. 6,051,378 (Monforte et al.), as well as PCT publications WO 98/26095 (Monforte et al.) and WO 97/27327 (Van Ness et al.).

In further embodiments, both electrochemical and infrared methods of detection can be amplified over the levels inherent to nucleic acid molecules through attachment of EC or IR labels. Their characteristics and use as labels are described in, for example, PCT publication WO 97/27327. Some preferred compounds that can serve as an IR label include an aromatic nitrile, aromatic alkynes, or aromatic azides. Numerous compounds can serve as an EC label; many are listed in PCT publication WO 97/27327.

Enzyme-linked reactions are also employed in the detecting step of the methods of the present invention. Enzyme-linked reactions theoretically yield an infinite signal, due to amplification of the signal by enzymatic activity. In this embodiment, an enzyme is linked to a secondary group that has a strong binding affinity to the molecule of interest. Following separation of the nucleic acid products, enzyme is bound via this affinity interaction. Nucleic acids are then detected by a chemical reaction catalyzed by the associated enzyme. Various coupling strategies are possible utilizing well-characterized interactions generally known in the art, such as those between biotin and avidin, an antibody and antigen, or a sugar and lectin. Various types of enzymes can be employed, generating colorimetric, fluorescent, chemiluminescent, phosphorescent, or other types of signals. As an illustration, a PCR primer may be synthesized containing a biotin molecule. After PCR amplification, DNA products are separated by size, and those made with the biotinylated primer are detected by binding with streptavidin that is covalently coupled to an enzyme, such as alkaline phosphatase. A subsequent chemical reaction is conducted, detecting bound enzyme by monitoring the reaction product. The secondary affinity group may also be coupled to an enzymatic substrate, which is detected by incubation with unbound enzyme. One of skill in the art can conceive of many possible variations on the different embodiments of detection methods described above.

In some embodiments, it may be desirable prior to detection to separate a subset of amplification products from other components in the reaction, including other products. Exploitation of known high-affinity biological interactions can provide a mechanism for physical capture. In some embodiments of this process, the 5' region of one of the universal primers contains a binding moiety that allows capture of the products of that primer. Some examples of high-affinity interactions include those between a hormone with its receptor, a sugar with a lectin, avidin and biotin, or an antigen with its antibody. After affinity capture, molecules are retrieved by cleavage, denaturation, or eluting with a competitor for binding, and then detected as usual by monitoring an associated label. In some embodiments, the binding interaction providing for capture may also serve as the mechanism of detection.

Furthermore, the size of an amplification product or products are optionally changed, or "shifted," in order to better resolve the amplification products from other products prior to detection. For example, chemically cleavable primers can be used in the amplification reaction. In this embodiment, one or more of the primers used in amplification contains a chemical linkage that can be broken, generating two separate fragments from the primer. Cleavage is performed after the amplification reaction, removing a fixed number of nucleotides from the 5' end of products made from that primer. Design and use of such primers is described in detail in, for example, PCT publication WO 96/37630.

One preferred embodiment of the methods of the present invention is the generation of gene expression profiles. However, several other applications are also possible, as would be apparent to one skilled in the art from a reading of this disclosure. For example, the methods of the present invention can be used to investigate the profile and expression levels of one or more members of complex gene families. As an illustration, cytochrome P-450 isozymes form a complex set of closely related enzymes that are involved in detoxification of foreign substances in the liver. The various isozymes in this family have been shown to be specific for different substrates. Design of target-specific primers that anneal to variant regions in the genes provides an assay by which their relative levels of induction in response to drug treatments can be monitored. Other examples include monitoring expression levels of alleles with allele-specific primers, or monitoring mRNA processing with primers that specifically hybridize to a spliced or unspliced region, or to splice variants. One skilled in the art could envision other applications of the present invention that would provide a method to monitor genetic variations or expression mechanisms.

Systems for Gene Expression Analysis

The present invention also provides systems for analyzing gene expression. The elements of the system include, but are not limited to, an amplification module for producing a plurality of amplification products from a pool of target sequences; a detection module for detecting one or more members of the plurality of amplification products and generating a set of gene expression data; and an analyzing module for organizing and/or analyzing the data points in the data set. Any or all of these modules can comprise high throughput technologies and/or systems.

The amplification module of the system of the present invention produces a plurality of amplification products from a pool of target sequences. The amplification module includes at least one pair of universal primers and at least one pair of target-specific primers for use in the amplification process. Optionally, the amplification module includes a unique pair of universal primers for each target sequence. Furthermore, the amplification module can include components to perform one or more of the following reactions: a polymerase chain reaction, a transcription-based amplification, a self-sustained sequence replication, a nucleic acid sequence based amplification, a ligase chain reaction, a ligase detection reaction, a strand displacement amplification, a repair chain reaction, a cyclic probe reaction, a rapid amplification of cDNA ends, an invader assay, a bridge amplification, a rolling circle amplification, solution phase and/or solid phase amplifications, and the like.

The detection module detects the presence, absence, or quantity of one or more members of the plurality of amplification products. Additionally, the detection module generates a set of gene expression data, generally in the form of a plurality of data points. The detection module optionally further comprises a separation module for separation of one or more members of the multiplexed reaction prior to, or during, operation of the detection module. The detection module, or the optional separation module, can include systems for implementing separation of the amplification products; exemplary detection modules include, but are not limited to, mass spectrometry instrumentation and electrophoretic devices.

The third component of the system of the present invention, the analyzing module, is in operational communication with the detection module. The analyzing module of the system includes, e.g., a computer or computer-readable medium having one or more one or more logical instructions for analyzing the plurality of data points generated by the detection system. The analyzing system optionally comprises multiple logical instructions; for example, the logical instructions can include one or more instructions which organize the plurality of data points into a database and one or more instructions which analyze the plurality of data points. The instructions can include software for performing difference analysis upon the plurality of data points. Additionally (or alternatively), the instructions can include or be embodied in software for generating a graphical representation of the plurality of data points. Optionally, the instructions can be embodied in system software which performs combinatorial analysis on the plurality of data points.

The computer employed in the analyzing module of the present invention can be, e.g., a PC (Intel x86 or Pentium chip-compatible DOS™, OS2™ WINDOWS™ WINDOWS NT™, WNDOWS95™, WINDOWS98™, or WINDOWS ME™), a LINUX based machine, a MACINTOSH™, Power PC, or a UNIX based machine (e.g., SUN™ work station) or other commercially common computer which is known to one of skill. Software for computational analysis is available, or can easily be constructed by one of skill using a standard programming language such as VisualBasic, Fortran, Basic, C, C++, Java, or the like. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can also be used in the analyzing system of the present invention.

The computer optionally includes a monitor that is often a cathode ray tube ("CRT") display, a flat panel display (e.g., active matrix liquid crystal display, liquid crystal display), or others. Computer circuitry is often placed in a box that includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for displaying and/or further analyzing raw data, massaged data, or proposed results from one or more computational processes involved in the analysis of the gene expression data set.

Kits

In an additional aspect, the present invention provides kits embodying the methods, compositions, and systems for analysis of gene expression as described herein. Kits of the present invention optionally comprise one or more of the following, preferably in a spatially separate arrangement: a) at least one pair of universal primers; b) at least one pair of target-specific primers; c) at least one pair of reference gene-specific primers; and d) one or more amplification reaction enzymes, reagents, or buffers. Optionally, the universal primers provided in the kit include labeled primers, such as those described in the present application and the references cited herein. The target-specific primers can vary from kit to kit, depending upon the specified target gene(s) to be investigated. Exemplary reference gene-specific primers (e.g., target-specific primers for directing transcription of one or more reference genes) include, but are not limited to, primers for β-actin, cyclophilin, GAPDH, and various rRNA molecules.

The kits of the invention optionally include one or more preselected primer sets that are specific for the genes to be amplified. The preselected primer sets optionally comprise one or more labeled nucleic acid primers, contained in suitable receptacles or containers. Exemplary labels include, but are not limited to, a fluorophore, a dye, a radiolabel, an enzyme tag, etc., that is linked to a nucleic acid primer itself.

In one embodiment, kits that are suitable for use in PCR are provided. In PCR kits, target-specific and universal primers are provided which include sequences that have sequences from, and hybridize to spatially distinct regions of one or more target genes. Optionally, pairs of target-specific primers are provided. Generally, the target-specific primers are composed of at least two parts: a universal sequence within the 5' portion that is complementary to a universal primer sequence, and a sequence within the 3' portion (and optionally, proximal to the universal sequence) for recognition of a target gene. In some embodiments of the invention, the set of targets monitored in an analysis may be specified by a client for use in a proprietary testing or screening application. In an alternate embodiment, standardized target sets may be developed for general applications, and constitute components of the kits described below. Kits of either of these embodiment can be used to amplify all genes, unknown and/or known, that respond to certain treatments or stimuli.

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

In one preferred embodiment of the invention, the kits are employed for analyzing gene expression patterns using mRNA as the starting template. The mRNA template may be presented as either total cellular RNA or isolated mRNA; both types of sample yield comparable results. In other embodiments, the methods and kits described in the present invention allow quantitation of other products of gene expression, including tRNA, rRNA, or other transcription products. In still further embodiments, other types of nucleic acids may serve as template in the assay, including genomic or extragenomic DNA, viral RNA or DNA, or nucleic acid polymers generated by non-replicative or artificial mechanism, including PNA or RNA/DNA copolymers.

Optionally, the kits of the present invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally comprise distinct containers for each individual reagent and enzyme, as well as for each probe or primer pair. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

EXAMPLES

The methods of the present invention are particularly suited for analyzing gene expression patterns. The present invention provides methods for the rapid generation of a differential expression profile of a defined set of genes through comparison of data from multiple reactions. Multiple differential expression profiles can be used for comparison of different cell types, or of a single cell type exposed to different environmental conditions, or in various developmental or disease states. The methods of the present invention provide a way to generate large bodies of differential expression data, which can be used for modeling a matrix of gene product interactions for whole cells. Relational analysis is used with large and complex sets of gene expression profiles, and is of valuable for identification of potential therapeutic targets, screening of candidate drugs, diagnostics, and other potential uses.

The methods of the present invention can also be suitably modified for the analysis of other biological processes, including, but not limited to, genotyping, mapping, mutation analysis, forensics, or analysis of other RNA molecules such as tRNAs, rRNAs, or hnRNAs.

The following examples are included to demonstrate various embodiments of the present invention. It will be appreciated by those of skill in the art that the techniques disclosed in the examples which follow represent techniques determined by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cell Culture and Chemical Exposure

The hepatocyte cell line, Hep G2 (human hepatocellular carcinoma, obtained from the American Type Culture Collection, Rockville Md., ATCC#HB-8065), was used to evaluate the effects of various chemicals on expression of a set of genes known to be involved in cellular toxicological responses. The cells were routinely maintained in T75 flasks in Eagle's MEM medium (with non-essential amino acids, sodium pyruvate, and Earle's salts) and 10% fetal bovine serum at 37° C. in a humidified atmosphere of 5% $CO_2$. The chemicals used in exposure experiments included cadmium chloride ($CdCl_2$) and methyl methane sulfonate (MMS). $CdCl_2$ is a strong inducer of metallothionein, a metalbinding protein, and is known to be carcinogenic and capable of interfering with DNA repair. MMS is an alkylating agent that induces DNA damage. Dilutions of these compounds were prepared from concentrated stocks obtained from Aldrich Chemical Company (Milwaukee, Wis.). Water was used as the solvent control in dosing studies. Approximately 0.02 mL of a dilution of each toxin was added to 2 mL of culture medium, with final concentrations ranging from 10-4M to 10-6M CdCl2 and from 0.5 mM to 2 mM MMS. These concentration ranges were empirically determined to not be lethal to cells for the duration of the exposure period. To perform exposures, cells were trypsinized and transferred to twelve-well dishes, seeding each well at a density of 1×104 cells/well. After 4 days of recovery and growth, cells were exposed to the designated toxin for 3 hours. Medium was then removed and cells immediately lysed. Cell number was quantitated using a dye incorporation assay, CyQUANT from Molecular Probes (Eugene, Oreg.).

Example 2

RNA Isolation

Total RNA was purified from crude cell lysates using Rneasy® total RNA purification kits from Qiagen Inc. (Valencia, Calif.), in an automation-compatible, 96-well format. In order to monitor recovery and stability of RNA from cell cultures, two purified RNA samples (Kanamycin Positive Control RNA from Promega (Madison, Wis.), and 7.5 kb Poly(A)-Tailed RNA from Life Technologies (Rockville, Md.)) were added with the lysis reagents. After the cellular treatments were complete, growth medium was removed and cells were lysed under denaturing conditions with RLT buffer (Qiagen, Valencia, Calif.) containing guanidine isothiocyanate and beta-mercapto ethanol to inactivate RNAses. Ethanol was then added to promote binding of RNA to the RNeasy membrane, and the entire volumes of the samples were loaded into the wells of a multiwell plate. The silica gel membrane of the RNeasy kit specifically binds total RNA, allowing contaminants to be washed away in flow-through processing of the membrane using a vacuum manifold. Samples bound to the membrane were dried by centrifugation of the plate. In order to elute RNA, 45 µL of RNAse-free water was added to each sample well, incubated, collected by centrifugation, and then the elution process repeated. Samples were stable in this form, and were stored at −80° C. for later use in expression assays.

Example 3

Reverse Transcription to Generate cDNA

A multiplex primer mix was designed to amplify ten target mRNAs, including four controls and six test targets. Two of the controls were endogenous cellular mRNAs that exhibit constant expression levels (β-actin and cyclophilin), allowing for normalization of signals from other genes. Two additional control RNA targets were added exogenously in the cell lysis buffer to provide a means to monitor recovery and stability of RNA from cell lysates (kanamycin mRNA and the 7.5 kb RNA as previously described). Six test genes were chosen that had been shown in prior art to exhibit changes in the amount of mRNA transcribed from those genes in response to a specific challenge.

Reverse transcription and PCR™ amplification primers were designed for the gene multiplex set using OLIGO 5.0 (Molecular Biology Insights, Inc., Cascade, Colo.). The sizes of the predicted PCR amplification products of the nine targets ranged from 100 to 330 bases, with the smallest size difference being 5 bases. The length of complementary sequence between each target-specific primer and its target sequence was 20 bases, and the length of complementary sequence between the target-specific primers and the universal primers was 18 bases. Primers were synthesized by Operon Technologies Inc. (Alameda, Calif.), or by chemists at GeneTrace Systems Inc. (Alameda, Calif.), utilizing conventional phosphoramidite synthesis techniques.

A mixture of reverse target-specific primers appropriate for the multiplex was prepared and diluted to a working concentration of 0.02 µM. (Reverse priming of β-actin mRNA is attenuated by addition of a second, inhibitory reverse target-specific primer. See Example 4.) To begin the reverse transcription step, 30 ng of total RNA, prepared as described in Example 2, was mixed with the reverse primers, 10 units of Moloney Murine Leukemia Virus Reverse Transcriptase (MoMLV-RT, Promega Inc.), and deoxyribonucleotides (1 mM from Promega) in an appropriate buffer (20 mM TrisHCl, 16.7 mM $MgCl_2$, pH 8.3, and 2.5 units RNasin). Samples were incubated at 42° C. for 30 minutes, followed by 95° C. for 5 minutes to inactivate the enzyme.

Example 4

Signal Attenuation

If one of the targets in a multiplex set is present at very high levels, it may be necessary to attenuate the signal generated by that target to ensure that all signals fall within the dynamic range of the assay. The β-actin mRNA provided one such example, as this mRNA is constitutively expressed at very high levels. Amplification of the β-actin signal was attenuated by using a mixture of two target-specific reverse primers, the first terminating at the 3' end with a hydroxyl group which is extendible by a reverse transcriptase, and the second containing a phosphate group attached to the 3'-hydroxyl which blocks extension by reverse transcriptase. The blocked β-actin primer was used in a 40-fold excess relative to the extendible primer, and the combined concentration was equivalent to the concentrations of all other target-specific reverse primers in the multiplex. This amount of inhibition typically resulted in about a 70% reduction in conversion of mRNA to cDNA.

Example 5

Multiplex Amplification of Target Sequences Using a Single, Unlabeled Universal Primer After inactivation of the reverse transcriptase, the cDNA products were used directly as templates in a PCR amplification. A mixture of forward target-specific primers appropriate for the multiplex reaction was prepared (SEQ ID No. 1–22). A single unlabeled universal primer was used for amplification; both the forward and reverse target-specific primers in the multiplex composition were designed to contain the same universal sequence within their 5' regions. The forward target-specific primers and the universal primer were diluted to a working concentration of 10 nM and 500 nM respectively, and then added to the samples from the reverse transcriptase reaction, along with 1 unit TaqGOLD® (Perkin-Elmer Applied Biosystems Inc., Foster City, Calif.) and 375 µM deoxyribonucleotides in an TaqGOLD-supplied buffer. The samples were heated at 95° C. for 10 minutes to activate the enzyme, then cycled at appropriate temperatures and for the appropriate number of cycles to achieve amplification of the designated target sequences, while remaining in the exponential phase of the reaction. For example, the samples are amplified for between 30–45 cycles using the following temperatures and times, 94° C. for 30 sec., 55° C. for 30 sec., and 68° C. for 1 min. See Innis, supra.

Example 6

Detection of Amplification Products by Mass Spectrometry

After PCR amplification, samples were ready for separation and analysis. The method of ionization used for mass spectrometric analysis was Matrix-Assisted Laser Desorption and Ionization (MALDI). Mass determinations were made by Time-of-Flight (TOF). A desorption/ionization matrix for analyzing samples was composed of a 9:1 ratio of saturated hydroxypicolinic acid (HPA) to picolinic acid (PA) (Aldrich) in 25% acetonitrile and 25 mM diammonium citrate. A mass spectrometer analysis plate was spotted in 384 positions with aliquots of the matrix, which were then allowed to dry and/or crystallize. A defined quantity of an oligonucleotide (e.g., 0.5 μl of a 5–10 μM solution, depending on the mass of the oligonucleotide), having a mass within the range of the amplification products, was added to each PCR reaction to serve as an internal quantitation standard. An aliquot of approximately 0.5–1 μl of each sample was then pipetted on top of each of the crystallized spots. Samples were allowed to dry again, forming DNA:HPA co-crystals.

The sample plate was placed in the mass spectrometer load lock chamber, pumped down to a low vacuum pressure, transferred to the sample chamber, then finally pumped down further to the required operating vacuum pressure. The sample chamber contains an X-Y table to orient the samples under the laser beam, and ion optics to accelerate and direct DNA ions into the flight tube and towards the detector. Ionized DNA fragments hitting the detector are assigned a mass based on the time required to travel through the flight tube. Various parameters were set within the automated data collection software to enable collection of signal in the appropriate mass range, and the coordinate positions on the analysis plate for the samples to be examined were entered. A laser beam of 355 nm light was focused through a window in the sample chamber onto the sample being analyzed. The laser power was adjusted to maximize the signal-to-noise ratio, while minimizing fragmentation of DNA in the sample. Data was collected according to the set parameters, generating a signal spectrum for each sample. The data was further processed using signal calling software proprietary to GeneTrace. The software smoothed the spectra, identified signal peaks, assigned masses to the peaks, and integrated the data to quantitate the relative amount of each species in the sample. These values were then normalized to the internal quantitation standard to convert the data to absolute values.

Data generated by the signal calling software was imported into Microsoft Excel (Bellevue, Wash.). Signals from each of the gene products being quantitated were normalized to the signal from the reference nucleic acid (the multiplex control target taken to have a constant abundance level). When a second reference target was included in the multiplex, this signal was also normalized to the first reference, and checked to confirm that its abundance relative to the first reference was constant. Data was stored in tabular form as normalized signal intensities.

Additional details regarding analysis by mass spectroscopy are presented in further examples as detailed below.

Example 7

Multiplex Amplification Using a Single, Labeled Forward Universal Primer and an Unlabeled Reverse Universal Primer The cDNA products of another toxicology multiplex sample were used as templates in a PCR amplification that generated labeled products. A mixture of forward target-specific primers appropriate for the multiplex reaction was prepared. These primers contained a different universal sequence within their 5' regions as that of the reverse primers used to generate the cDNA. A forward universal primer was modified by covalent attachment of a fluorescein moiety (FAM, available from Perkin-Elmer/Applied Biosystems, Inc.), while the reverse universal primer remained unlabeled. The forward target-specific primers and the universal primers were diluted to a working concentration and then added to samples from the reverse transcriptase reaction, along with TaqGOLD and deoxyribonucleotides in an appropriate buffer. The PCR amplification was carried out as described in Example 5.

Example 8

Generating a Pool of Two Multiplexed Amplifications—Using a Single Forward Universal Primer Containing One of Two Labels and an Unlabeled Reverse Universal Primer The cDNA products of additional toxicology multiplex samples were used as templates in two PCR amplifications to generate differently labeled products. A mixture of forward target-specific primers appropriate for the multiplex reaction was prepared. These primers contained a different universal sequence within their 5' regions as that of the reverse primers used to generate the cDNA. In addition to the fluorescein-modified primer described in Example 2, a second preparation of the forward universal primer was made, modifying it by covalent attachment of a hexachlorofluorescein moiety (HEX, Perkin-Elmer/Applied Biosystems, Inc.). The reverse universal primer remained unlabeled. The forward target-specific primers and the universal primers were diluted to a working concentration (of 10 nM and 500 nM respectively). Forward target-specific primers, TaqGOLD and deoxyribonucleotides in an appropriate buffer were added to samples from the reverse transcriptase reaction. The FAM-modified forward universal primer was added to one of the PCR amplification reactions, and the HEX-modified forward universal primer was added to the other. PCR amplification was carried out as described in Example 5.

Example 9

Detection of Amplification Products by Polyacrylamide Gel Electrophoresis

After PCR amplification using the fluorescently-labeled primers, the multiplexed samples were ready for analysis by polyacrylamide gel electrophoresis. A standard sequencing gel composed of 5% polyacrylamide, and containing 6M urea and 890 mM Tris-borate and 2 mM EDTA, was cast for use on an ABI PRISM 377 DNA Sequencer (Perkin-Elmer/ Applied Biosystems). Amplification products were diluted and mixed with a solution of GeneScan 500 ROX-labeled size standards (PE Applied Biosystems, California) in formamide (1:5). Samples were loaded on the gel, and the components of the multiplex reaction mixture were electrophoretically separated by size according to standard conditions, for example, 1.5 hours running at 2000 V, 60 mA current, 20 W power, gel temperature of 51° C., and laser power of 40 mW (ABI 377). Fluorescent data was collected by laser scanning across the gel in real time. GeneScan™ software was used to quantitate fluorescent signals from the amplification products, and Genotyper™ software (both from Perkin-Elmer/Applied Biosystems) was used for subsequent calculations and data manipulations.

Example 10

Generating a Pool of Two Multiplexed Amplifications—Using Two Forward Universal Primers of Different Lengths and with Different Labels, and an Unlabeled Reverse Universal Primer The cDNA products of other toxicology multiplex samples were used as template in two PCR amplifications to generate equivalent amplification products of slightly offset sizes, both labeled with the same chromaphore. A mixture of forward target-specific primers appropriate for the multiplex was prepared. These primers contained a different universal sequence at their 5' ends as that of the reverse primers used to generate the cDNA. Two forward universal primers were made with the same universal sequence, but one contained three additional bases at its 5' end. One of the forward universal primers was modified by covalent attachment of a FAM moiety, and the other was modified by covalent attachment of a HEX moiety. The reverse universal primer remained unlabeled. The forward target-specific primers and the universal primers were diluted to a working concentration. Forward target-specific primers, TaqGOLD and deoxyribonucleotides in an appropriate buffer were added to samples from the reverse transcriptase reaction. One of the labeled forward universal primers was added to each of the reactions. PCR amplification was carried out as described in Example 4.

Example 11

Detection of Amplification Products by Denaturing Capillary Electrophoresis

Two PCR multiplex samples are analyzed by capillary electrophoresis at the end of the PCR amplification. The samples were combined, diluted 1:10 in CE sample dilution buffer (1:5 dilution of fluorescently labeled ladder in deionized formamide). The pooled sample was analyzed on an ABI PRISM 310 Genetic Analyzer, with capillaries containing POP4 acrylamide matrix (PE Perkin-Elmer Applied Biosystems, CA). Components of the pooled multiplexes were electrophoretically separated by size according to standard conditions. Fluorescent data was collected at wavelengths appropriate for the FAM and HEX labels. Sizes were assigned to each signal peak based on their migration relative to the ROX size standards.

Example 12

Data Analysis

The data collected from the FAM and HEX fluorescent signals were analyzed using GeneScan analysis software. The fluorescent signals were deconvoluted to yield information specific for each of the individual fluorophores in the mixture, to generate a baseline, to sort the signals into "size bins" relative to the ROX size standards, and to quantitate the amount of DNA represented in each bin. The results from this analysis were further processed by Genotyper software (PE Applied Biosystems, CA) to automate the repetitive tasks of data analysis. Sample files from GeneScan were imported into Genotyper, which then assigned data to the size ranges programmed by the operator. The data generated in this manner was stored in tabular form, and then imported into Excel. The signals from each of the gene products being quantitated were normalized to the signal generated by the internal reference (the multiplex control target taken to have a constant abundance level). When a second internal reference target was included in the multiplex, this signal was also normalized to the first reference, and checked to confirm that its abundance relative to the first reference was constant. Data was stored in tabular form as normalized signal intensities.

Example 13

Multiplex Analysis of Cellular Transcription in PC-3 Cells after Treatment with Battery of Compounds Preparation of Target Sequences PC-3, a human prostate adenocarcinoma cell line (American Type Culture Collection, Rockville, Md.) was cultured in T-225 $cm^2$ flasks (Corning Costar Corp., Cambridge, Mass.) using Kaighn's Nutrient Mixture F-12 (Irvine Scientific, Santa Ana, Calif.) containing 7% fetal bovine serum (FBS) (Hyclone, Logan, Utah) and 1 mM L-glutamine. The cell culture reagents were obtained from Gibco BRL Life Technologies (Grand Island, N.Y.) except where otherwise noted. Cells were maintained at 37° C. in a humidified cell incubator containing 5% $CO_2$. At approximately 70% confluence, the growth media was aspirated and cells were rinsed with D-PBS. Cells were harvested by trypsinization, treated with trypan blue exclusion viability stain and counted using a hemacytometer. Lidded 96-well microtiter culture plates (Becton Dickinson, Franklin Lakes, N.J.) were then seeded at $5 \times 10^4$ cells per well in a 200 µL media volume. Two wells were left empty to allow the later addition of external process controls. Seeded plates were incubated for 3 hours (37° C., 5% $CO_2$, in a humidified cell incubator) to allow for cell attachment prior to compound addition.

A set of 80 known drugs ("Killer Plate 1", from MicroSource Discovery Systems, Inc., Gaylordsville, Conn.) and an actinomycin-D positive control were solubilized in 100% DMSO (Sigma Chemical Co., St. Louis, Mo.) and diluted to 8× working solutions with growth media prior to cell plate addition. Compounds from a chemical library (in pooled format) and subsequent confirmation of individual compound activities were analyzed at a final concentration of 2.5 µM in 0.25% DMSO. Positive and vehicle control wells were maintained at 0.25% DMSO (v/v) which had no effect on cell growth or gene targets. For dose-response analysis, compounds were plated in triplicate and analyzed using eight concentrations (between 10 µM and 3.16 nM in 0.25% DMSO), as prepared by serial dilution. After cell attachment was verified by phase contrast microscopy, a 25 µL aliquot of media was removed from the cell plate and an equivalent volume of compound working solution (8×) was introduced with mild trituration of the well volume, using a MultiMek 96 pipetting station (Beckman Coulter, Fullerton, Calif.). Cell plates were then returned to the incubator for a 24 hour exposure period.

Lysis buffer was prepared by adding 145 mM β-mercaptoethanol (Sigma Chemical Co., St. Louis, Mo.) and external mRNA controls (to a final concentration of 500 fM) to RLT Lysis buffer (Qiagen, Valencia, Calif.). Two external mRNA controls were used: 7.5 kb poly(A)-tailed RNA and 1.2 kb Kanamycin Positive Control, which were treated with DNAse to ensure that no contaminating DNA was present. Following a 24 hour incubation period, cell media was aspirated from all wells using an EL-404 plate washer (BioTek Instruments, Winooski, Vt.). Lysis buffer (100 μL) was pipetted into each well containing cells. Plates were then mixed on an orbital shaker (Labline, Melrose Park, Ill.) for 15 seconds. Adhesive aluminum foil strips (E&K Scientific, Campbell, Calif.) were used to seal the plates prior to frozen storage at −20° C.

For gene expression analysis, the cell lysates were thawed, and total RNA was purified in automated 96-well format using the Qiagen RNeasy 96 kit according to the manufacturer's recommended procedure. RNA concentrations were determined fluorometrically using RiboGreen reagent (Molecular Probes, Eugene, Oreg.), adjusted in concentration, and aliquoted in 30 ng amounts into 96-well plates for assay. Total RNA yields ranged from 0.45 to 1.8 μg per well depending on compound toxicity. RNA samples were verified to be free from DNA contamination by running controls in which MMLV reverse transcriptase enzyme was omitted from the multiplex assay protocol. Purified RNA controls were included on each plate for process quality control and tracking.

Primer Design

Assay specificity was determined by utilizing unique primers for each gene. Target-specific primers were designed to six target sequences and two reference sequences (Table 1). Both forward-TSPs and reverse TSPs were synthesized, having sequences as delineated in Table 2. The 5' region of the target-specific sequences includes sequences complementary to one of two universal sequences

TABLE 1

Target-Specific Primers for Multiplexed Analysis of Gene Expression in PC-3 cells

| Target Sequence | F-primer | R-primer | Size (bp) |
|---|---|---|---|
| beta-actin | Sp61F | T7(P7)R3/R3pi (1:39) | 117 |
| cloning vector lambda EMBL3 SP6/T7 fragment in GibcoBRL 7.5 kp mRNA | Sp6(P2)F2 | T7(P7)R2 | 127 |
| INAD | Sp6F1 (P2) | T7R1 (P7) | 147 |
| hSPE | Sp6F2 (P2) | T7R2 (P7) | 157 |
| survivin | Sp6F1 (&F2) (P2) | T7R2 (P7) | 200 |
| HNF 3 alpha | Sp6F3 (P2) | T7R3 (P7) | 215 |
| GAPDH | Sp6F1 (P2) | T7R1 (P7) | 237 |
| EST | Sp6(P2)F4 | T7(P7)R4 | 266 |
| Hoxb 13 | Sp6F1 (P2) | T7R1(&R2) (P7) | 283 |
| (KanR) aminoglycoside 3'-phosphotransferase | Sp6(P2)(LP70)F2 | T7(P7)R2 | 322 |

TABLE 2

Target-Specific Primer Sequences (SEQ ID NOS 1-22, respectively in order of appearance)

| Accession # | Primer | Primer Name | Primer Sequence |
|---|---|---|---|
| X00351 | β-actin forward | Sp6.1F1 | AGGTGACACTATAGAATAACCGAT AAGGCCAACCGCGAGAAGATGA |
| X00351 | β-actin reverse | T77R3 | GTACGACTCACTATAGGGATGGAT AGCAACGTACATGGCTG |
| X00351 | β-actin reverse Phosphorylated | T77R3Pi | GTACGACTCACTATAGGGATGGAT AGCAACGTACATGGCTGPi |
| U02426 fragment | 7.5 kb forward | Sp6(P2)F2 | AGGTGACACTATAGAATAACTATG CCGGTATCAGCACC |
| U02426 fragment | 7.5 kb reverse | T7(P7)R2 | GTACGACTCACTATAGGGAGATGG CAGCGTGATTTCAC |
| INA D | INA D forward | Sp6F1 (P2) | AGGTGACACTATAGAATAGTGACA CGTCGCAGAATGAG |
| INA D | INA D reverse | T7R1 (P7) | GTACGACTCACTATAGGGATTGAC CCTTCAGTTGCTTGA |
| hSPE | hSPE forward | Sp6F2 (P2) | AGGTGACACTATAGAATAGCTTCA TTAGGTGGCTCAACA |
| hSPE | hSPE reverse | T7R2 (P7) | GTACGACTCACTATAGGGAGGCTC AGCTTGTCGTAGTTC |
| Survivin | Survivin forward | Sp6F1(&F2) (P2) | AGGTGACACTATAGAATAGTCAGC CCAACCTTCACATC |
| Survivin | Survivin reverse | T7R2 (P7) | GTACGACTCACTATAGGGACCACC CTGCAGCTCTATGAC |
| HNF 3 alpha | HNF 3 alpha forward | Sp6F3 (P2) | AGGTGACACTATAGAATAACTTCA AGGCATACGAACAG |
| HNF 3 alpha | HNF 3 alpha reverse | T7R3 (P7) | GTACGACTCACTATAGGGAGGGAG CTAGGAAGTGTTTAG |
| | GAPDH | | AGGTGACACTATAGAATAAAGGTG |

TABLE 2-continued

Target-Specific Primer Sequences (SEQ ID NOS 1-22,
respectively in order of appearance)

| Accession # | Primer | Primer Name | Primer Sequence |
|---|---|---|---|
| M33197 | forward | Sp6F1 (P2) | AAGGTCGGAGTCAA GTACGACTCACTATAGGGAATGAC |
| M33197 | GAPDH reverse | T7R1 (P7) | AAGCTTCCCGTTCTC GTACGACTCACTATAGGGAATGAC |
| M33197 | GAPDH reverse phosphorylated | T7R1Pi (P7) | AAGCTTCCCGTTCTCPi AGGTGACACTATAGAATAGCTCAT |
| EST | EST forward | Sp6F4 (P2) | CTGCCAACAATC GTACGACTCACTATAGGGACTAGC |
| EST | EST reverse | T7R4 (P7) | GGAAGCAAATTACAC AGGTGACACTATAGAATAGCGACA |
| Hoxb 13 | Hoxb 13 forward | Sp6F1 (P2) | TGACTCCCTGTT GTACGACTCACTATAGGGAAACTT |
| Hoxb 13 | Hoxb 13 reverse | T7R1(&R2) (P7) | GTTAGCCGCATACTC |
| J01839 (V00359) | KanR forward | Sp6(P2)(LP70) F2 | AGGTGACACTATAGAATAATCATC AGCATTGCATTCGATTCCTGTTTG |
| J01839 (V00359) | KanR reverse | T7(P7)R2 | TACGACTCACTATAGGGAATTCCG ACTCGTCCAACATC |

Preparation of Primer Sequences

Oligonucleotides were prepared using phosphoramidite methodology on an ABI 394 DNA synthesizer using standard procedures and reagents, including dG$^{dmf}$ FastPhosphoramidite (PE Biosystems 401183), 0.02M Iodine (PE Biosystems 401732) as oxidant, and 0.25M 5-ethyl-1H-tetrazole (Glen Research 30-3140-52) as activator. 5'-biotinylated nucleotides were incorporated using commercially available amidite reagents as described in the procedure below. Preparation of the cleavable primer sequences involved the synthesis of a protected 3' thiothymidine reagent (5'-O-Dimethoxytrityl-3'-thiothymidine-3'-S-(2-cyanoethyl)-N,N-diisopropyl phosphorothioamidite). The 3'-thiothymidine nucleotide was incorporated in an automated fashion using the protected phosphoramidite reagent described above. Column chromatography was carried out under a positive pressure of argon gas. HPLC data were collected on an Hewlett-Packard 1100 series instrument at 260 nm.

In cases where mass spectrometric analysis was performed, one universal primer of each target-specific primer pair was prepared having a biotin moiety incorporated at the 5'-end, and a chemically-cleavable base, 3'-thiothymidine at an appropriate position. Cleavage of the amplified PCR product at the position of the 3'-thiothymidine reduces the measured DNA size, thus providing fragments suitable for optimal mass spectral resolution and sensitivity. Furthermore, the cleavable bases could be introduced in various positions within different universal primers used in different multiplex reactions. The various cleaved positions yield a series of non-overlapping mass spectral peaks suitable for multiplexed readout.

5'-biotin phosphoramidite (Glen Research 10-5950-90, 0.1M in anhydrous acetonitrile) and Thio-T amidite (0.1M in anhydrous acetonitrile) were employed in the synthesis of the universal primers. The synthesis was carried out using a 10-minute coupling time for Biotin and a two 5-minute couplings for Thio-T. The crude oligonucleotide was deprotected in 28% aqueous NH3 at 55° C. for two hours. Removal of the solvent gave a white residue that was desalted on a NAP-10 column (Pharmacia 17-0854-01) with ddH2O. The product was analyzed by HPLC using a Supelcosil LC-18-T column (Supelco 58971) and a gradient of 10 to 20% acetonitrile from 5 to 25 min. at 1 mL per min. in 0.1M TEAA. Typical retention times were about 10 to 15 min., and the purity of the product should exceed 80%.

For cases where the samples were analyzed on a fluorescence electrophoretic device, a universal primer was synthesized that included a dye at the 5' end. Fluorescent dye labeling of primers with 6-FAM was carried out on an automated DNA synthesis device using 5'-fluorescein phosphoramidite (Glen Research, Sterling, Va.).

"Shifted" Universal Primers

Greater assay throughput is achieved by mixing PCR products of the original gene set (i.e. target sequences) with a "shifted" gene set so that signals from the products of the two gene sets are interleaved. The "shifted" genes are separated from the original genes by the same number of bases for each product in the multiplexed gene set. The "shifted" genesets are generated by the addition of nucleotides to the labeled strand of the universal primer to increase the length of the PCR products. Spacers are used to separate the label from the specific portion of the universal primer sequence.

Shifted target universal primers were synthesized that contained a nonnucleotide linker. The nonnucleotide linker used was an abasic nucleotide, dSpacer phosphoramidite, 5;-dimethoxytrityl-1,2-dideoxyribose-3'-cyanoethyl phosphoramidite (Glen Research, Sterling, Va.) The dSpacer was incorporated during automated DNA synthesis on a DNA synthesis device using standard methods. After incorporation of the dSpacer between 1 to 10 thymidine bases were incorporated and optionally a dye label was also added.

For example, the universal primers used in a first series of multiplex amplifications to generate an original geneset comprises a FAM-labeled Sp6 universal sequence (forward direction) and an unlabeled T7 universal sequence (reverse direction)

Labeled Sp6; 5'-(FAM)-AGG TGA CAC TAT AGA
ATA-3'                                     (SEQ ID No. 23)

Non-labeled T7; 5'-GTA CGA CTC ACT ATA
GGG A-3'                                   (SEQ ID No. 24)

Alternatively,the T7 sequence can carry the fluorescent label while the Sp6 sequence is unlabelled:

Non-labeled Sp6: (SEQ ID NO: 23) 5'-AGG TGA CAC TAT AGA
ATA-3'

Labeled T7: (SEQ ID NO: 24) 5'(FAM)-GTA CGA CTC ACT
ATA GGG A-3'

In a second set of multiplex amplifications, universal primers containing additional nucleotides are employed (dS=dSpacer phosphoramidite, available from Glen Research, Sterling Va.), such that the molecular weight or mass of the resulting amplified sequences is altered as compared to the first series of amplification reactions. Exemplary universal primers for generation of the shifted geneset are:

Labeled Sp6: (SEQ ID NO: 25) 5'-(FAM)-TTTTTTT-dS*-AGG TGA CAC TAT AGA ATA-3'

Non-labeled T7: (SEQ ID NO: 24) 5'-GTA CGA CTC ACT ATA GGG A-3'

As with the primers used in the previously-described amplification reaction, the label can be carried on either of the universal sequences employed:

Non-labeled Sp6: (SEQ ID NO: 23) 5'-AGG TGA CAC TAT AGA ATA-3'

Labeled T7: (SEQ ID NO: 26) 5'-(FAM)-TTTTTTT-dS*-GTA CGA CTC ACT ATA GGG A-3'

Reactions may also be performed separately for the same set of target sequences using multiple dyes, which are then mixed to increase throughput. Labeled universal primers are also "shifted" in size to avoid overlapping peaks and for improved reproducibility. All reactions using multiple dyes were performed with the same non-labeled T7 universal primers. Exemplary labeled Sp6 universal primers include:

FAM-labeled Sp6: (SEQ ID NO: 23) 5'-(FAM)-AGG TGA CAC TAT AGA ATA-3'

HEX-labeled Sp6: (SEQ ID NO: 27) 5'-(HEX)-TAG AGG TGA CAC TAT AGA ATA-3' or (SEQ IN NO: 28) 5'-(HEX)-TTT-(dS)-AGG TGA CAC TAT AGA ATA-3'

NED-labeled Sp6: (SEQ ID NO: 29) 5'-(NED)-GAT TAG AGG TGA CAC TAT AGA ATA-3'

Additional primers can be designed by one of skill in the art. For example, reactions may also be performed where one of the universal primers contains a cleavable site and optionally a biotin, for specific solid-phase capture. Cleavable universal primers are "shifted" in size once they are cleaved. As an example, all reactions using cleavable Sp6 primers were performed with a non-labeled T7 universal primer. Exemplary labeled Sp6 universal primers include:

Cleavable Sp6: (SEQ ID NO: 30) 5'-(Biotin)-AGG TGA CAC TAthioT AGA ATA-3'

Amplification

The multiplex amplification step utilized solution-phase quantitative multiplex RT-PCR amplification, and was coupled with multiplexed fluorescence or mass spectrometric detection. Primer pairs (SEQ ID Nos. 1–22) for specific genes and controls were designed using Primer-3 software (Whitehead Institute for Biomedical Research, Cambridge, Mas.).

Reverse transcription to generate first strand cDNA was carried out using 30 ng of total RNA, 0.02 μM primers, 1 mM dNTPs, RNasin ribonuclease inhibitor (2.5 units, Promega, Madison, Wis.), and MMLV reverse transcriptase (10 units, Promega, Madison, Wis.) at 42° C. for 30 minutes. PCR amplifications were performed using 0.01 μM gene-specific primers, 1 μM universal primers, 0.375 mM dNTPs (Promega, Madison, Wis.), and AmpliTaq Gold polymerase (1 unit, Perkin Elmer, Foster City, Calif.) in the buffer supplied with the enzyme. Thermal cycling was performed on a Perkin-Elmer GeneAmp 9700 between 30 to 45 cycles using the following conditions: 94° C. for 30 s, 55° C. for 30 s and 68° C. for 1 minute. Multiplex PCR products were resolved using either the electrophoresis or capillary systems for fluorescent readout when they were all in the linear range of amplification, and were quantified by fluorescence intensity. For fluorescent readout, one of the universal primer pairs used for PCR amplification was labeled with the fluorescent dye 6-FAM utilizing 5'-fluorescein phosphoramidite (Glen Research, Sterling, Va.).

Gel electrophoresis

The samples were prepared for multiplex fluorescent readout using a gel electrophoresis system from The Gel Company (San Francisco, Calif.) by diluting the RT-PCR products 1:4 in GE sample dilution buffer (a 1:3.3 dilution of fluorescently labeled ladder (CXR Fluorescent Ladder, Promega, Madison, Wis.), 1:16 dilution of blue dextran, and 1:1.6 dilution of deionized formamide). The fluorescent ladder was used as a gel standard with every sample for normalization of the target PCR product sizes. After denaturing the samples at 95° C. for 5 minutes and cooling in ice-water bath for 5 minutes, 0.5 μL of the diluted RT-PCR samples were loaded onto a 96-well linear loading tray and transferred via absorption onto a 96-lane paper comb. The comb was then inserted onto the gel and samples were allowed to run into the gel for approximately 35 seconds, after which the comb is removed and discarded.

Capillary electrophoresis

RT-PCR products for multiplex fluorescent readout using the capillary electrophoresis system were diluted 1:10 in CE sample dilution buffer (1:5 dilution of fluorescently labeled ladder in deionized formamide). Approximately 10 μl of the diluted T-PCR samples were placed in receptacles specific for the capillary electrophoresis instrument and denatured at 95° C. for 5 minutes. The samples were then cooled for 5 minutes in ice-water bath prior to performing the capillary electrophoresis.

Mass spectroscopic analysis

Subsequent to PCR amplification, samples were processed to prepare them for mass spectrometric analysis. The processing steps were conducted in 384-well plates on a robotic workdeck containing a magnetic platform to facilitate manipulation and washing of magnetic beads.

Streptavidin-coated magnetic beads were added to each sample in binding solution, 10 mM Tris, 20 mM ammonium acetate, 1 mM EDTA buffer, pH 7.2, and incubated at room temperature for 20 minutes to allow binding of the biotinylated primer. The sample tray was placed on a magnet platform of a robotic workstation to precipitate the DNA bound to the beads. After the beads were pelleted, the supernatant was removed, and the pellet was rinsed once with binding solution.

A denaturing solution of 0.1N NaOH was used to rinse the pelleted beads and to remove the non-biotinylated complementary strand. A second aliquot of the denaturing added, mixed above the pelleted beads, then incubated. The mixing process was repeated four times, then the final supernatant was removed. The beads were washed five times with a 20 mM ammonium acetate solution, then twice with deionized water to remove residual salts. The beads were then resuspended in a cleavage solution (0.1 mM silver nitrate) and the samples were incubated at 48° C. for 15 minutes. The tray was returned to the workstation to precipitate the beads, and the supernatant was transferred to a fresh 384-well tray. A solution of 70 mM DTT solution was added to samples in the new tray to quench the reaction, and samples were dried in a vacuum centrifuge.

Approximately 0.5 mL of a matrix solution consisting of a 5:1 molar ratio of 3-hydroxypicolinic acid (3-HPA) to picolinic acid (PA) was added to each well containing dried sample. The matrix solution was prepared by mixing 18 $\mu$L of a freshly prepared saturated 3-HPA solution (about.0.5 M) with 2 $\mu$L of 1 M PA. The redissolved samples were then spotted (either manually or robotically) onto a mass spectrometer sample plate, 0.5 $\mu$l, and allowed to crystallize for subsequent analysis.

For mass spectrometry readout, a linear time-of-flight (TOF) mass spectrometer was employed, using an acceleration voltage of +20 kV; delay of +3.6 kV at 1.12 $\mu$sec; laser setting of 179 on the polarizer; mass gate of 5.84 $\mu$sec; and 400 shots. Furthermore, a 2-point mass calibration with a 15-mer (4507.0 Da) and a 36-mer (10998.2 Da) was utilized.

Quantitative levels of all genes in each sample, including target and external spike control genes, were normalized to the internal controls, and are expressed as ratios to the control ("housekeeping") genes GAPDH and $\beta$-actin.

Validation of Primer Design

Multiplexed amplifications were validated to ensure that each primer pair was specific for a particular target sequence and that there were no interactions among the target sequences in the multiplex. This was accomplished by conducting drop-out experiments, in which the multiplex amplification was run in the absence of a particular primer pair. Additionally, the amplification reaction was validated by comparing the results of primers in different multiplex environments, ensuring identical PCR product sizes in each case. Furthermore, primers were also tested for efficiency by running the multiplex assay on RNA samples known to express all of the targeted sequences.

Example 14

Multiplex Strategies

Table 3 depicts exemplary strategies for multiplexing samples in the methods of the present invention. Multiplex reactions A and B illustrate fundamental multiplexing strategies for use in the methods of the present invention. In these assays, all of the forward universal primers (UPfs) include the same universal sequence; in addition, a single type of dye label is incorporated into the primers. In multiplex reaction A, the reverse universal primers (UPrs) all have the same sequence with each other, but a different sequence from the forward universal primers. The reverse universal primers do not have an incorporated dye. In multiplex reaction B, all of the forward universal primers and reverse universal primers contain the same sequence, and therefore both strands of the products will have an incorporated dye. In the given example, at the end of each type of reaction, the multiplexed samples contain 12 strands of amplified products (two complementary strands from each of six templates), with dye incorporated in either half (for example A) or all (multiplex reaction B) of the strands. Because the dye is the same for all targets, detection of individual products depends on their separation (in this case, based on size).

Multiplex reaction C depicts an embodiment in which semi-universal primers are used to shift the mobility of a subset of the amplification products during size separation of otherwise overlapping peaks. Two forward universal primers are used for designated subsets of targets. Both primers are labeled with the same dye, but one of them additionally contains a friction group (i.e., an attached moiety that generates drag on molecules as they migrate through a non-matrixed, liquid solution). See, for example, Hubert and Slater (1995) Electrophoresis 16:2137–2142. In this example, the sizes of products 1 and 4, 2 and 5, and 3 and 6 are the same or overlapping, but corresponding peaks 1, 2, and 3, as well as 4, 5, and 6 are different sizes. The friction group will be incorporated into products 4, 5, and 6, while leaving products 1, 2, and 3 unmodified. As a result, the mobilities of products 4–6 will be retarded relative to 1–3, resolving these otherwise overlapping sets into six separate peaks. The illustration represents the reverse universal primers as all being the same sequence, but these primers may also comprise a set of semi-universal primers.

Multiplex reaction D illustrates another embodiment of the components of the multiplex reaction which can be employed in order to resolve overlapping signals. In this reaction profile, two amplification products of the multiplex are the same size. The mobility of one of the two overlapping signals can be shifted by adding a nucleic acid sequence to one or both of the TSPs for one of the target sequences, lengthening its amplification product. A similar effect is obtained by designing semi-universal primers of different sizes.

Multiplex reaction E illustrates an important embodiment of the methods of the present invention, which provides a mechanism by which the signals for multiple species are resolved by separating other than by size. A set of semi-universal primers is employed in the multiplex reaction; each UPf is labeled with one of a set of independent labels, each of which can be detected uniquely. As with multiplex reaction C, the sizes of products 1 and 4, 2 and 5, and 3 and 6 are taken as the same or overlapping, but peaks 1, 2, and 3, as well as 4, 5, and 6 are different sizes. Products 1–3 will be labeled with dye number 1, and products 4–6 with dye number 2. The two sets of three products will still have overlapping mobilities, but the fluorescent signals given by each of the two dyes can now be separated by deconvolution of the emission spectral data. As in the previous example, the UPrs can also be designed as semi-universal primers.

Multiplex reaction F illustrates a method for obtaining signals from a greater number of unresolved species than the number of available dyes. Two dyes were used in the multiplex illustration of multiplex reaction E, enabling resolution of two overlapping signals. In the embodiment described in multiplex reaction E, the signal from three unresolved products are obtained using only two dyes with three different UPf primers. In this embodiment, the third signal is obtained by double-labeling the amplification products of that target. Because the signal from this product is known to contain an equivalent fluorescent signal from each of the two dyes, its signal can be separated from the signals of the two singly-labeled products. This application requires that the three types of products are not completely overlapping, which would make deconvolution of their signals very difficult. Ideally, the signals from the two singly-labeled species should not overlap, but some overlap can be resolved by signal processing of the data. More complex combinations are obviously possible when more than two dyes are used.

These six cases are provided for illustration of the more important embodiments of multiplexing reactions described in this invention. To one skilled in the art, many variations in multiplexing strategies are possible by combining separate elements of these examples. In particular, combination strategies can be employed making use of the separate forward and reverse universal primers, or the combinations of target-specific and universal primers, or semi-universal primers. In all cases, the selection of the particular TSP sequences for each target within a multiplex can be performed carefully to select the size of each PCR product and ensure that each product can be detected uniquely.

Optionally, the methods of the present invention include methods to increase the number of samples simultaneously analyzed by pooling the products of separate reactions. This strategy increases the throughput and reduces the cost of the assay for situations in which the pooled products cannot be generated in the same reaction (for example, when each separate reaction is already maximized in multiplexing potential). For example, samples are pooled after the RT-PCR reaction is complete, and prior to analysis and quantitation.

(For examples G through M, it is assumed for illustration that all of the products of each separate multiplex are resolvable by size.) As an example, each separate reaction may be performed with the same UPf primer, labeled with the same chromaphore. After the reaction, the samples are combined for analysis. All of the individual signals from the two reactions are then resolved by size.

The embodiments provided in Cases H-L illustrate various ways of resolving the same set of amplified sequences generated in separate reactions. Multiplex reaction H illustrates the use of isotopic or chemical modification to generate shifts in the masses of otherwise equivalent amplification products. For example, deuterated dNTPs may be used to generate "heavy" amplification products (designated as sequence $A^H$ in reaction H2) in one reaction, while unmodified dNTPs are used in another (reaction H1). The

TABLE 3

Multiplexing Strategies for the RT-PCR

| Example | UPf | UPf label | UPr | UPr label | Application |
|---|---|---|---|---|---|
| A | UPf 1–6 = sequence "A" | dye #1 | UPr 1–6 = sequence "B" | none | Resolution of a simple multiplex by size (two universal primers) |
| B | UPf 1–6 = sequence "A" | dye #1 | UPr 1–6 = sequence "A" | dye #1 | Resolution of a simple multiplex by size (one universal primer) |
| C | UPf 1–3 set, sequence "A" + UPf 4–6 set, sequence "A" | dye #1 dye #1 + friction group | UPr 1–6 = sequence "B" | none | Use semi-universal primers to create resolution by affecting mobility Create resolution by size shifting (where amplification products 1–3 have overlapping masses with products 4–6) |
| D | UPf 1–6 = sequence "A" | dye #1 | UPr 1–6 = sequence "B" | none | Create resolution by shifting size (TSP length was changed to shift the mass of it's amplicon) |
| E | UPf 1–3 = sequence "A" UPf 4–6 set, sequence "B" | dye #1 dye #2 | UPr 1–6 = sequence "C" | none | Use semi-universal primers to resolve by size & fluorescence (multiplexing with dyes) |
| F | UPf 1 = sequence "A" + UPf2 = sequence "B" + UPf3 = sequence "C" | dye #1 dyes #1 and 2 (50:50) dye #2 | UPr 1–6 = sequence "D" | none | Increase dye multiplexing capacity possible with a fixed number of dyes |

Example 15

Pooling of Samples Using Interleaving Genesets or Multiple Dyes

RT-PCR samples for the same multiplexed reaction may be mixed at appropriate ratios by combining either the original set of target sequences with the "shifted" target sequence set, and/or by combining reactions with multiple dyes. These mixed samples are then diluted in the appropriate sample dilution buffer and loaded onto the gel or capillary electrophoresis system. Exemplary profiles of original and "shifted" multiplex genesets are shown in FIG. 4. Examples of profiles generated by multiplexed amplification with different dyes using multiplex genesets are shown in FIG. 5. Several illustrations of pooling strategies are listed in Table 4, and described below.

Multiplex reaction G illustrates an embodiment of a fundamental pooling strategy for use in the methods of the present invention. In this example, two separate reactions (G1 and G2) comprise different multiplexes. The combined products of the two separate reactions are resolvable by size.

heavier deuterium isotopes of hydrogen that are incorporated in one set of reaction products will generate a shift in the mass of each product relative to the equivalent amplicon of the other reaction.

The embodiment illustrated with multiplex reaction I makes use of the friction molecules described previously in multiplex reaction C. In multiplex reaction I, two reactions (I1 and I2) of the same multiplex set are performed, the first with unmodified UPf primers and the second with UPf primers containing a friction group. Both primers are labeled with the same dye. After the reaction, samples are combined for analysis. The friction group will be incorporated into all of the products of reaction I2. As a result, the otherwise overlapping signals will be separated by the frictional drag of one species relative to the other.

Multiplex reaction J provides a way for detecting duplicate multiplex sets by a mass shift. In this embodiment, two UPf primers are used, one of which is shorter (in reaction J1) than the other (reaction J2). Two separate reactions are conducted, each using different universal primers. This will result in a duplicate signal pattern in which one group is offset from the other by a fixed size. This size offset can also be accomplished by using two UPf primers coupled with two UPr primers, and changing the lengths of one pair of UPf and UPr primers by a lesser amount.

FIG. 4 depicts exemplary detection profiles of original and "shifted" multiplex genesets, as prepared by methods of the present invention. The position of the signal along the X-axis generally correlates with number of nucleotides in the amplified product, while the Y axis indicates intensity of fluorescent signal. Panel A represents data as collected for an "original" geneset, while panel B depicts data for a "shifted" geneset (for which, in this example, the amplified products appear to have a greater mass or friction coefficient as compared to the unmodified amplification sequences). Panel C presents the original and shifted genesets together, demonstrating the resolution introduced into the products of the "shifted" amplification reaction.

Multiplex reaction K illustrates a pooling strategy based on a mass shift between duplicate multiplex sets, just as with multiplex reaction J. In this illustration primers of the same sequence and length are used for both multiplexes. However, for one of the reactions (K2), the UPf incorporates a site of cleavage between two nucleotides in the extension product. (Thus, the label must be incorporated 3' to the cleavage site in order for it to remain with the extension product). After amplification is complete, the products made with the modified primer are cleaved, removing a fixed number of nucleotides from the 5' end of the labeled strand. Cleavage may be performed after pooling of separate reactions. Cleavage sites can be situated in one of several positions in a primer sequence, facilitating pooling of multiple reactions.

In the embodiment illustrated in multiplex reaction L, identical multiplexed reactions are generated (reactions L1, L2 and L3). Rather than mixing the reactions prior to loading on the separation platform, they are simply loaded individually, but with time delays, in order to generate an offset in their relative positions in the separation medium.

Multiplex reaction M illustrates the use of multiple labels, e.g. fluorescent dyes, each of which can be uniquely detected. In this embodiment, three separate reactions (M1, M2 and M3) are performed with a single UPf primer sequence, but that contains one of three different labels. After the reaction, the three samples are combined for analysis. Each particular target from each reaction will have the same size as those from each of the other reactions. The triplicate sets of signals from the three reactions will be resolved by deconvolution of the fluorescence data. Examples of profiles generated by multiplexed amplification with different dyes using multiplex genesets are shown in FIG. 5. The position of the signal along the X-axis correlates with number of nucleotides in the amplified product, while the Y axis indicates intensity of fluorescent signal. Panel A=FAM-labeled products; panel B=HEX-labeled products; panel C=NED-labeled products; and panel D=FAM, HEX, & NED-labeled products combined. As with all other case illustrations, the UPr primers can be utilized in conjunction with the UPf primers to design more complex strategies.

TABLE 4

Pooling Strategies for Analysis

| Reaction | UPf (product) | Label | UPr (product) | Label | Application |
|---|---|---|---|---|---|
| G1 | UPf 1–6 (seq A) | dye #1 | UPr 1–6 (seq B) | none | Resolution by size. |
| G2 | UPf 7–12 (seq B) | dye #1 | UPr 7–12 (seq B) | none | |
| H1 | UPf 1–6 (seq A) | dye #1 | UPr 1–6 (seq B) | none | Separate reactions have relative mobility shifts from use of different |
| H2 | UPf 1–6 (seq A$^H$) | dye #1 | UPr 1–6 (seq B) | none | isotopes |
| I1 | UPf 1–6 (seq A) | dye #1 | UPr 1–6 (seq B) | none | Separate reactions have relative mobility shifts resulting from the |
| I2 | UPf 1–6 (seq A) | dye #1 + friction group | UPr 1–6 (seq B) | none | "friction" group. (Note: product masses of the two reactions overlap) |
| J1 | TSP f, set #1 (seq A) | dye #1 | UPr 1–6 (seq B) | none | Separate reactions have relative mass offsets resulting from primer |
| J2 | TSP f, set #2 (seq A + 5 bases) | dye #1 | UPr 7–12 (seq B) | none | length differences. |
| K1 | UPf 1–6 (seq A) | dye #1 | UPr 1–6 (seq B) | none | Separate reactions have relative mobility shifts resulting from |
| K2 | UPf 1–6 (seq A + cleavage site) | dye #1 | UPr 1–6 (seq B) | none | removal of nucleotides by cleavage within the primer. |
| L1 | UPf 1–6 (seq A) | dye #1 | UPr 1–6 (seq B) | none | Separate reactions have relative mobility shifts resulting from |
| L2 | UPf 1–6 (seq A) | dye #1 | UPr 1–6 (seq B) | none | staggered sample loading on the separation platform |
| L3 | UPf 1–6 (seq A) | dye #1 | UPr 1–6 (seq B) | none | |
| M1 | UPf 1–6 (seq A) | dye #1 | UPr 1–6 (seq B) | none | Three separate reactions are pooled for analysis. Resolution by size & |

TABLE 4-continued

Pooling Strategies for Analysis

| Reaction | UPf (product) | Label | UPr (product) | Label | Application |
|---|---|---|---|---|---|
| M2 | UPf 1–6 (seq A) | dye #2 | UPr 1–6 (seq B) | none | fluorescence (multiplexing with dyes). (Note: products masses of the three reactions overlap.) |
| M3 | UPf 1–6 (seq A) | dye #3 | UPr 1–6 (seq B) | none | |

Note: "Product" refers to the amplification product; product seq $A^H$ represents a "heavy" version of seq A

TABLE 5

PRIMER SEQUENCES

| SEQ ID No. | Accession # | Primer | Primer Name | Primer Sequence |
|---|---|---|---|---|
| SEQ ID No 1 | X00351 | beta-actin forward | Sp6.1F1 | AGGTGACACTATAGAATAACCGA TAAGGCCAACCGCGAGAAGATGA |
| SEQ ID No. 2 | X00351 | beta-actin reverse | T77R3 | GTACGACTCACTATAGGGATGGA TAGCAACGTACATGGCTG |
| SEQ ID No. 3 | X00351 | beta-actin reverse Phosphorylated | T77R3Pi | GTACGACTCACTATAGGGATGGA TAGCAACGTACATGGCTGPi |
| SEQ ID No. 4 | U02426 | 7.5 kb forward fragment | Sp6(P2)F2 | AGGTGACACTATAGAATAACTAT GCCGGTATCAGCACC |
| SEQ ID No. 5 | U02426 | 7.5 kb reverse fragment | T7(P7)R2 | GTACGACTCACTATAGGGAGATG GCAGCGTGATTTCAC |
| SEQ ID No. 6 | n/a | INA D forward | Sp6F1 (P2) | AGGTGACACTATAGAATAGTGAC ACGTCGCAGAATGAG |
| SEQ ID No. 7 | n/a | INA D reverse | T7R1 (P7) | GTACGACTCACTATAGGGATTGA CCCTTCAGTTGCTTGA |
| SEQ ID No. 8 | n/a | hSPE forward | Sp6F2 (P2) | AGGTGACACTATAGAATAGCTTC ATTAGGTGGCTCAACA |
| SEQ ID No. 9 | n/a | hSPE reverse | T7R2 (P7) | GTACGACTCACTATAGGGAGGCT CAGCTTGTCGTAGTTC |
| SEQ ID No. 10 | n/a | Survivin forward | Sp6F1(&F2) | AGGTGACACTATAGAATAGTCAG CCCAACCTTCACATC |
| SEQ ID No. 11 | n/a | Survivin reverse | T7R2 (P7) | GTACGACTCACTATAGGGACCAC CCTGCAGCTCTATGAC |
| SEQ ID No. 12 | n/a | HNF 3 alpha forward | Sp6F3 (P2) | AGGTGACACTATAGAATAACTTC AAGGCATACGAACAG |
| SEQ ID No. 13 | n/a | HNF 3 alpha reverse | T7R3 (P7) | GTACGACTCACTATAGGGAGGGA GCTAGGAAGTGTTTAG |
| SEQ ID No. 14 | M33197 | GAPDH forward | Sp6F1 (P2) | AGGTGACACTATAGAATAAAGGT GAAGGTCGGAGTCAA |
| SEQ ID No. 15 | M33197 | GAPDH reverse | T7R1 (P7) | GTACGACTCACTATAGGGAATGA CAAGCTTCCCGTTCTC |
| SEQ ID No. 16 | M33197 | GAPDH reverse phosphorylated | T7R1Pi (P7) | GTACGACTCACTATAGGGAATGA CAAGCTTCCCGTTCTCPi |
| SEQ ID No. 17 | n/a | EST forward | Sp6F4 (P2) | AGGTGACACTATAGAATAGCTCA TCTGCCAACAATC |
| SEQ ID No. 18 | n/a | EST reverse | T7R4 (P7) | GTACGACTCACTATAGGGACTAG CGGAAGCAAATTACAC |
| SEQ ID No. 19 | n/a | Hoxb 13 forward | Sp6F1 (P2) | AGGTGACACTATAGAATAGCGAC ATGACTCCCTGTT |
| SEQ ID No. 20 | n/a | Hoxb 13 reverse | T7R1(&R2) (P7) | GTACGACTCACTATAGGGAAACT TGTTAGCCGCATACTC |
| SEQ ID No. 21 | J01839 (V00359) | KanR forward | Sp6(P2)(LP70)F2 | AGGTGACACTATAGAATAATCAT CAGCATTGCATTCGATTCCTGTTT G |
| SEQ ID No. 22 | J01839 (V00359) | KanR reverse | T7(P7)R2 | TACGACTCACTATAGGGAATTCC GACTCGTCCAACATC |
| SEQ ID No. 23 | n/a | Sp6 | universal primer | AGGTGACACTATAGAATA |
| SEQ ID No. 24 | n/a | T7 | universal primer | GTACGACTCACTATAGGGA |

The cases described above are provided for illustrative purposes. One skilled in the art can envision other embodiments that would achieve the general purpose of increasing sample throughput during separation and data collection.

While the foregoing invention has been described in some detail for purposes of clarity and understanding, it will be clear to one skilled in the art from a reading of this disclosure that various changes in form and detail can be made without departing from the true scope of the present invention. For example, all the techniques and compositions described above may be used in various combinations. All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for analyzing gene expression comprising:
   a) obtaining a plurality of target sequences, wherein the plurality of target sequences comprises cDNA;
   b) multiplex amplifying said plurality of target sequences, wherein multiplex amplifying comprises combining the plurality of target sequences, a plurality of target-specific primers, and one or more universal primers, and wherein the universal primer is provided in an excess concentration relative to the target-specific primer, thereby producing a plurality of amplification products;
   c) separating one or more members of the plurality of amplification products;
   d) detecting one or more members of the plurality of amplification products, thereby generating a set of gene expression data;
   e) storing the set of gene expression data in a database; and
   f) performing a comparative analysis on the set of gene expression data, thereby analyzing the gene expression.

2. The method of claim 1, wherein a universal primer:target-specific primer concentration ratio ranges from about 5:1 to about 100:1.

3. The method of claim 1, wherein a universal primer:target-specific primer concentration ratio is about 10:1.

4. A method for analyzing gene expression comprising:
   a) obtaining a plurality of target sequences, wherein the plurality of target sequences comprises cDNA;
   b) multiplex amplifying said plurality of target sequences, wherein multiplex amplifying comprises combining the plurality of target sequences, a plurality of target-specific primers, and one or more universal primers, wherein an annealing temperature of the universal primer is higher than an annealing temperature of the target-specific primer; thereby producing a plurality of amplification products;
   c) separating one or more members of the plurality of amplification products;
   d) detecting one or more members of the plurality of amplification products, thereby generating a set of gene expression data;
   e) storing the set of gene expression data in a database; and
   f) performing a comparative analysis on the set of gene expression data, thereby analyzing the gene expression.

5. A method for analyzing gene expression comprising:
   a) obtaining a plurality of target sequences, wherein the plurality of target sequences comprises cDNA;
   b) multiplex amplifying said plurality of target sequences, wherein multiplex amplifying comprises combining the plurality of target sequences, a plurality of target-specific primers, and one or more universal primers, and wherein multiplex amplifying the cDNA further comprises attenuating an amplification of abundant target genes, thereby producing a plurality of amplification products;
   c) separating one or more members of the plurality of amplification products;
   d) detecting one or more members of the plurality of amplification products, thereby generating a set of gene expression data;
   e) storing the set of gene expression data in a database; and
   f) performing a comparative analysis on the set of gene expression data, thereby analyzing the gene expression.

6. The method of claim 5, wherein attenuating the amplification of abundant target genes comprises using one or more modified target-specific primers.

7. The method of claim 6, wherein the one or more modified target-specific primer comprises a blocking group attached at a 3' end of the modified target-specific primer.

8. The method of claim 6, wherein the one or more modified target-specific primer comprises one or more abasic nucleotides or mismatch nucleotides.

9. The method of claim 6, wherein using one or more modified target-specific primers comprises providing a mixture of the one or more modified target-specific primers with one or more unmodified target-specific primers, at a ratio optimized for a desired amount of attenuation.

10. The method of claim 6, wherein the one or more modified target-specific primer comprises a blocking group attached at a 3' end of a reverse target-specific primer.

11. The method of claim 6, wherein the one or more modified target-specific primers comprise primers having a phosphate group on the terminal 3'-hydroxyl of the target-specific primer.

12. The method of claim 6, wherein the one or more modified target-specific primers comprise primers having a nucleotide penultimate to the terminal 3'-nucleotide and attached via a 3'-3' phosphodiester linkage.

13. The method of claim 1, 4 or 7, wherein obtaining the target sequences comprises performing reverse transcription of mRNA.

14. The method of claim 13, wherein the mRNA comprises mRNA derived from cultured cells.

15. The method of claim 13, wherein said mRNA comprises mRNA derived from cultured cells subjected to a specific treatment.

16. The method of claim 15, wherein said specific treatment comprises a chemical exposure, an environmental stress, or an exposure to one or more viable organisms or cells.

17. The method of claim 1, 4 or 5, wherein multiplex amplifying comprises simultaneously amplifying a plurality of cDNA in the same reaction mixture; wherein said plurality of target-specific primers comprises one or more target-specific primer pairs, each pair comprising a forward target-specific primer and a reverse target-specific primer; and wherein the one or more universal primers comprises one or more universal primer pairs, each pair comprising a forward universal primer and a reverse universal primer.

18. The method of claim 1, 4 or 5, wherein said plurality of target sequences further comprises one or more reference sequences, wherein a portion of the one or more reference sequences is homologous to at least one member of the plurality of target-specific primers.

19. The method of claim 18, wherein one or more of the reference sequences comprises sequences endogenously present in the cDNA.

20. The method of claim 18, wherein one or more of the reference sequences comprises sequences exogenously added to the cDNA.

21. The method of claim 1, 4 or 5, wherein at least one member of the plurality of target-specific primers or universal primers further comprises a modified nucleotide.

22. The method of claim 21, wherein the modified nucleotide prevents amplification of one or more portions of the at least one member of the plurality of target-specific primers or universal primers.

23. The method of claim 21, wherein the modified nucleotide comprises one or more non-nucleotide linkers, alkyl chains, or abasic nucleotides.

24. The method of claim 1, 4 or 5, wherein at least one member of the plurality of target-specific primers or universal primers further comprises a cleavable linker.

25. The method of claim 1, 4 or 5, wherein at least one universal primer further comprises a label.

26. The method of claim 25, wherein the label comprises one or more of a chromaphore, a fluorophore, a dye, a releasable label, a mass label, an affinity label, a friction moiety, a hydrophobic group, or an isotopic label.

27. The method of claim 1, 4 or 5, wherein each member of the plurality of target-specific primers comprises a first sequence that is derived from a target gene of interest and positioned within a 3' region of the member, and a second sequence that is complementary to the universal primer and positioned within a 5' region of the member.

28. The method of claim 1, 4 or 5, wherein the one or more universal primers comprise one or more semi-universal primers.

29. The method of claim 28, wherein each of the one or more semi-universal primers comprises a unique label.

30. The method of claim 28, wherein the one or more semi-universal primers comprise primers which are complementary to one or more forward target-specific primers, one or more reverse target-specific primers, or a combination thereof.

31. The method of claim 30, wherein the one or more semi-universal primers comprise a first semi-universal primer that is complementary to all of the one or more forward target-specific primers, and a second semi-universal primer that is complementary to all of the one or more reverse target-specific primers.

32. The method of claim 1, 4 or 5, wherein obtaining a plurality of target sequences comprises providing two or more target sequences having two or more target-specific primer annealing temperatures.

33. The method of claim 1, 4 or 5, wherein multiplex amplifying the cDNA comprises amplifying target genes that have comparable expression levels.

34. The method of claim 1, 4 or 5, wherein multiplex amplifying further comprises altering the length of one or more of the universal primers or one or more of the plurality of target-specific primers prior to combining.

35. The method of claim 34, wherein altering the length comprises adding nucleotides to an end of a universal primer or a target-specific primer.

36. The method of claim 34, wherein altering the length comprises incorporating a non-nucleotide linker into a universal primer or a target-specific primer.

37. The method of claim 34, wherein altering the length comprises cleaving the one or more universal primers or the one or more target-specific primers.

38. The method of claim 34, wherein one or more of the universal primers or one or more of the plurality of target-specific primers comprise semi-universal primers.

39. The method of claim 34, wherein altering the length comprises inserting nucleotides within a universal primer or a target-specific primer.

40. The method of claim 39, wherein altering the length of a target-specific primer comprises inserting nucleotides between a universal sequence and a target-specific sequence of the target-specific primer.

41. The method of claim 1, 4 or 5, wherein the plurality of amplification products comprises a plurality of labels at predetermined molar ratios.

42. The method of claim 41, wherein the plurality of labels is incorporated on a single oligonucleotide primer.

43. The method of claim 41, wherein the plurality of labels is incorporated on a plurality of oligonucleotide primers.

44. The method of claim 1, 4 or 5, wherein separating the one or more members of the plurality of amplification products comprises performing one or more size separation techniques.

45. The method of claim 44, wherein separating the one or more members of the plurality of amplification products comprises performing HPLC or FPLC.

46. The method of claim 44, wherein separating the one or more members of the plurality of amplification products comprises performing mass spectrometry.

47. The method of claim 44, wherein separating the one or more members of the plurality of amplification products comprises employing an electrophoresis platform.

48. The method of claim 47, wherein the electrophoresis platform comprises one or more of a capillary platform, a microcapillary platform, a microfluidics platform, an agarose gel, an acrylamide gel, an agarose/acrylamide gel or a chromatographic platform.

49. The method of claim 1, 4 or 5, wherein performing the comparative analysis comprises measuring a ratio of each target gene to each reference gene.

50. The method of claim 1, 4 or 5, wherein separating the one or more members of the plurality of amplification products comprises performing HPLC followed by mass spectroscopy.

51. The method of claim 1, 4 or 5, wherein detecting the one or more members of the plurality of amplification products comprises measuring one or more inherent properties of the amplification products.

52. The method of claim 51, wherein the one or more inherent properties comprise mass, light absorption, or an electrochemical property.

53. The method of claim 1, 4 or 5, wherein detecting the one or more members of the plurality of amplification products comprises measuring the presence, absence, or quantity of a labeled amplification product.

54. The method of claim 53, wherein the labeled amplification product comprises a singly labeled amplification product, a multiply-labeled amplification product, or a combination thereof.

55. The method of claim 53, wherein detecting comprises resolving a first signal from a singly labeled amplification product and a second signal from a multiply labeled amplification product by deconvolution of the data.

56. The method of claim 53, wherein detecting comprises resolving a first signal from a singly labeled amplification product and a second signal from a multiply labeled amplification product by reciprocal subtraction of the first or second signal from an overlapping signal.

57. The method of claim 1, 4 or 5, wherein one or more of the multiplex amplifying, separating and detecting is performed in a high throughput format.

58. A method for analyzing gene expression comprising:
   a) obtaining cDNA from a plurality of samples for a plurality of target sequences;
   b) performing a plurality of multiplexed amplifications of the target sequences, thereby producing a plurality of multiplexed amplification products, wherein performing a multiplexed amplification comprises combining a plurality of target sequences, one or more target-specific primers, and one or more universal primers to form a reaction mixture, and wherein the reaction mixture comprises one or more of i) an excess concentration of the one or more universal primers relative to a target-specific primer, ii) universal primers which have a higher annealing temperature relative to the annealing temperature of a target-specific primer, or iii) modified target-specific primer for attenuation of abundant target genes;
   c) pooling the plurality of multiplexed amplification products;
   d) separating the plurality of multiplexed amplification products;
   e) detecting the plurality of multiplexed amplification products, thereby generating a set of gene expression data;
   f) storing the set of gene expression data in a database; and
   g) performing a comparative analysis of the set of gene expression data.

59. The method of claim 58, wherein at least one of the one or more universal primers or one or more target-specific primers comprises a label.

60. The method of claim 59, wherein the first or second label comprises a high-affinity intercalating dye.

61. The method of claim 59, wherein a first multiplexed amplification is performed with a primer comprising a first label that produces a first signal, and a second multiplexed amplification is performed with a primer comprising a second label that produces a second signal, wherein the first and second signals are distinguishable from one another.

62. The method of claim 61, wherein the first and second signals are distinguishable by deconvolution of signals obtained from the plurality of multiplexed amplification products.

63. The method of claim 58, wherein performing the plurality of amplifications of the target sequences comprises using universal primers having two or more lengths, and wherein detecting the plurality of multiplexed amplification products comprises measuring one or more size shifts among the plurality of multiplexed amplification products.

64. The method of claim 58, wherein performing the plurality of amplifications of the target sequences comprises using target-specific primers having two or more lengths, and wherein detecting the plurality of multiplexed amplification products comprises measuring one or more size shifts among the plurality of multiplexed amplification products.

65. The method of claim 64, performing the plurality of amplifications of the target sequences comprises using universal primers comprising one or more cleavage sites, and wherein detecting the plurality of multiplexed amplification products comprises measuring one or more size shifts among the plurality of multiplexed amplification products.

66. The method of claim 58, wherein separating the plurality of multiplexed amplification products comprises shifting the mobility of member amplification products relative to one another.

67. The method of claim 66, wherein shifting the mobility comprises incorporating a friction moiety into one or more of the universal primers, thereby creating a reduction in mobility of the amplification products.

68. The method of claim 58, wherein separating comprises applying each set of multiplex amplification products to a separation platform at different times.

69. The method of claim 58, wherein performing the plurality of amplifications comprises performing a polymerase chain reaction, a transcription-based amplification, a self-sustained sequence replication, a nucleic acid sequence based amplification, a ligase chain reaction, a ligase detection reaction, a strand displacement amplification, a repair chain reaction, a cyclic probe reaction, a rapid amplification of cDNA ends, an invader assay, a solid phase assay, a solution phase assay, or a combination thereof.

70. The method of claim 69, wherein the solid phase assay comprises a bridge amplification or rolling circle amplification.

71. The method of claim 58, wherein one or more of the performing, separating and detecting is performed in a high throughput format.

72. The method of claim 71, wherein one or more of the performing, separating and detecting steps is performed at a rate of about 1000 samples per hour.

73. A method for analyzing gene expression comprising:
   a) obtaining cDNA from multiple samples;
   b) amplifying a plurality of target sequences from the cDNA, thereby producing a multiplex set of amplification products, wherein amplifying the plurality of target sequences comprises combining the plurality of target sequences, one or more target-specific primers, and one or more universal primers to form a reaction mixture, and wherein the reaction mixture comprises one or more of i) an excess concentration of the one or more universal primers relative to a target-specific primer, ii) universal primers which have a higher annealing temperature relative to the annealing temperature of a target-specific primer, or iii) modified target-specific primer for attenuation of abundant target genes;
   c) separating and detecting the amplification products using a high throughput platform, wherein detecting generates a set of gene expression data; and
   d) storing the set of gene expression data in a database; and
   e) performing a comparative analysis of the set of gene expression data.

74. The method of claim 73, wherein the one or more universal primers or the one or more target-specific primers comprise one or more non-nucleotide linkers.

75. The method of claim 73, wherein separating and detecting the amplification products comprises performing mass spectrometry, polyacrylamide gel electrophoresis, HPLC, capillary electrophoresis, microcapillary electrophoresis, or a combination thereof.

76. The method of claim 73, wherein separating and detecting the amplification products is performed using microfluidic devices.

77. The method of claim 73, wherein the high throughput platform comprises an HPLC for separating the amplification products and a mass spectrometer for detecting the amplification products.

78. The method of claim 73, wherein the high throughput platform comprises one or more miniaturized scale platforms.

79. The method of claim 73, wherein one or more of the amplifying, separating and detecting steps is performed at a rate of about 100 samples per hour to about 5,000 samples per hour.

80. The method of claim 73, wherein one or more of the amplifying, separating and detecting steps is performed at a rate of about 1000 samples per hour.

81. The method of claim 73, wherein amplifying the plurality of target sequences comprises performing on or more of a polymerase chain reaction, a transcription-based amplification, a self-sustained sequence replication, a nucleic acid sequence based amplification, a ligase chain reaction, a ligase detection reaction, a strand displacement amplification, a repair chain reaction, a cyclic probe reaction, a rapid amplification of cDNA ends, an invader assay, a solution phase amplification assay, or a solid phase amplification assay.

82. The method of claim 81, wherein the solid phase amplification assay comprises a bridge amplification or rolling circle amplification.

* * * * *

SEQUENCE LISTING

<160> NUMBER OF SEQ ID NOS: 30

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 1
aggtgacact atagaataac cgataaggcc aaccgcgaga agatga            46

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 2
gtacgactca ctatagggat ggatagcaac gtacatggct g                 41

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Primer
<223> OTHER INFORMATION: 3' Phosphorylated

<400> SEQUENCE: 3
gtacgactca ctatagggat ggatagcaac gtacatggct g                 41

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 4
aggtgacact atagaataac tatgccggta tcagcacc                     38

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 5
gtacgactca ctatagggag atggcagcgt gatttcac                     38

```
<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 6
aggtgacact atagaatagt gacacgtcgc agaatgag                           38

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 7
gtacgactca ctatagggat tgacccttca gttgcttga                          39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 8
aggtgacact atagaatagc ttcattaggt ggctcaaca                          39

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 9
gtacgactca ctatagggag gctcagcttg tcgtagttc                          39

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 10
aggtgacact atagaatagt cagcccaacc ttcacatc                           38

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 11
gtacgactca ctatagggac caccctgcag ctctatgac                          39

<210> SEQ ID NO 12
<211> LENGTH: 38
<212> TYPE: DNA
<213> ORGANISM: Artificial Sequence
<220> FEATURE:
```

<223> OTHER INFORMATION: Description of Artificial Sequence: Primer

<400> SEQUENCE: 12
aggtgacact atagaataac ttcaaggcat acgaacag         38

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 13
gtacgactca ctagggag ggagctagga agtgtttag         39

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 14
aggtgacact atagaataaa ggtgaaggtc ggagtcaa         38

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 15
gtacgactca ctagggaa tgacaagctt cccgttctc         39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Primer
<223> OTHER INFORMATION: 3' Phosphorylated

<400> SEQUENCE: 16
gtacgactca ctagggaa tgacaagctt cccgttctc         39

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 17
aggtgacact atagaatagc tcatctgcca acaatc         36

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 18
gtacgactca ctagggac tagcggaagc aaattacac         39

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 19
aggtgacact atagaatagc gacatgactc cctgtt                                36

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 20
gtacgactca ctatagggaa acttgttagc cgcatactc                             39

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 21
aggtgacact atagaataat catcagcatt gcattcgatt cctgtttg                   48

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 22
tacgactcac tatagggaat tccgactcgt ccaacatc                              38

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 23
aggtgacact atagaata                                                    18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 24
gtacgactca ctataggga                                                   19

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Primer
<223> OTHER INFORMATION: 5' FAM-labeled
<223> OTHER INFORMATION: dSpacer phosphoramidite between position 7 and
    8

<400> SEQUENCE: 25
tttttttagg tgacactata gaata                                          25

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Primer
<223> OTHER INFORMATION: 5' FAM-labeled
<223> OTHER INFORMATION: dSpacer phosphoramidite between position 7 and
    8

<400> SEQUENCE: 26
tttttttgta cgactcacta taggga                                         26

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Primer
<223> OTHER INFORMATION: 5' HEX-labeled

<400> SEQUENCE: 27
tagaggtgac actatagaat a                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer
<223> OTHER INFORMATION: 5' HEX-labeled
<223> OTHER INFORMATION: dSpacer phosphoramidite between position 3 and
    4

<400> SEQUENCE: 28
tttaggtgac actatagaat a                                              21

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Primer
<223> OTHER INFORMATION: 5' NED-labeled

<400> SEQUENCE: 29
gattagaggt gacactatag aata                                           24

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Primer
<223> OTHER INFORMATION: 5' Biotin-labeled
<221> NAME/KEY: modified_base -continued

```
<222> LOCATION: (12)
<223> OTHER INFORMATION: Thio-T amidite

<400> SEQUENCE: 30
aggtgacact atagaata                                                      18
```